United States Patent [19]

Ishida

[11] Patent Number: 4,667,017

[45] Date of Patent: May 19, 1987

[54] METHOD FOR PRODUCING AN ACTIVE PROTEIN

[75] Inventor: Torao Ishida, Nagareyama, Japan

[73] Assignee: Asahi Kasei Kogyo Kabushiki Kaisha, Osaka, Japan

[21] Appl. No.: 640,819

[22] Filed: Aug. 15, 1984

[30] Foreign Application Priority Data

Aug. 15, 1983 [JP] Japan ................................ 58-148026

[51] Int. Cl.$^{4}$ ................................................ C07K 1/02

[52] U.S. Cl. .................................... 530/402; 530/339

[58] Field of Search ................. 260/112.5 R; 530/402, 530/339

[56] References Cited

PUBLICATIONS

Nature vol. 281 (1979) 544–548.

Proc. Nat'l. Acad. Sci. vol. 76, (1979) 106–110.

"Chem. Pharm. Bull.", 29 (2), 600–602 (1981).

Balogh et al., "Journal of the American Chemical Society", 101, 751–752 (1979).

Hitzeman et al., "Science", 219, 620–625 (1983).

Itakura et al., "Science", 209, 1401–1405 (1980).

*Primary Examiner*—Delbert R. Phillips

*Attorney, Agent, or Firm*—Birch, Stewart, Kolasch & Birch

[57] ABSTRACT

An active protein can be easily, safely produced by a method comprising providing a first peptide fragment having a first amino acid sequence corresponding to part of an active protein and a second peptide fragment having a second amino acid sequence corresponding to the remaining part of the active protein, at least one of said first peptide fragment and said second peptide fragment being one which has been obtained by recombinant DNA technique or has been obtained by a method comprising producing a predetermined peptide fragment by recombinant DNA technique and deleting from or adding to said predetermined peptide fragment at its N-terminus at least one amino acid residue; and linking said first peptide fragment at its C-terminus to said second peptide fragment at its N-terminus. The method of the present invention may be practiced, with further advantages, by predeterming said first peptide fragment and said second peptide fragment so that a first occurring methionine residue subsequent to the N-terminal amino acid residue of the active protein constitutes the N-terminal amino acid of the amino acid sequence of said second peptide fragment, or so that an amino acid residue positioned near the first occurring methionine residue subsequent to the N-terminal amino acid residue of the desired protein on the side of the N-terminus of the desired protein constitutes the N-terminal amino acid residue of said second peptide fragment.

15 Claims, No Drawings

METHOD FOR PRODUCING AN ACTIVE PROTEIN

BACKGROUND OF THE INVENTION

This invention relates to a novel method for producing an active protein. More particularly, the present invention is concerned with the production of an active protein by linking two peptide fragments, at least one of said two peptide fragments being one which has been obtained by recombinant DNA technique or has been obtained by a method comprising producing a predetermined peptide fragment by recombinant DNA technique and deleting from or adding to said predetermined peptide fragment at its N-terminus at least one amino acid residue. By this method, there can be easily, safely obtained a desired active protein in a skillful manner.

The term "active protein" used herein means a protein of a three dimentional structure which comprises 60 or more of amino acid residues and exhibits a physiological activity.

In recent years, there have been established the structures of various physiologically active peptides, and studies have been made in the art to synthesize such active peptides. Such peptides may be classified, according to the number of amino acid residues constituting the peptide, into oligopeptides (2 to about 10 amino acid residues), polypeptides (about 10 to about 60 amino acid residues) and proteins (about 60 or more amino acid residues) and, therefore, oligopeptides, polypeptides and proteins used in the present specification mean such peptides as classified above.

In 1881, the synthesis of a dipeptide, the smallest peptide, was reported [T. Curtius, J. Pract. Chem., 24, 239 (1881)]. Since then, various attempts to produce peptides were made. In 1969, bovine RNase A was organochemically synthesized by a solid phase method [B. Gutte and R. B. Merrifield, Journal of American Chemical Society, 91, 501 (1969)] but the end product was not obtained in pure form. On the other hand, H. Yajima and N. Fujii succeeded in organic synthesis of bovine RNase A by a liquid phase method after the study of a period of time as long as three and a half years [H. Yajima and N. Fujii, Chemical and Pharmaceutical Bulletin, 29, 600 (1981)].

In spite of the success of Yajima et al., techniques have not yet progressed to an extent that proteins are easily synthesized. In general, the technique of organic synthesis for a protein is on the extension of the method of E. Fisher, Berichte Deutsche Chemische Gesellschaft, 40, 1754 (1907). According to the general technique, however, extremely increasing difficulties will be encountered in the synthesis of a protein with the increase of size of the protein. Polypeptides differ from proteins mainly in size and properties. Although the synthesis of proteins is an extension of the synthesis of polypeptides, difficulties not accompanying the synthesis of polypeptides, for example, the synthesis of human insulin *P. Sieber et al., Helv. Chim. Acta.*, 57, 2617 (1974)] are encountered in the synthesis of proteins. In the liquid phase method, a long chain peptide of which the functional groups are entirely or partially protected usually becomes sparingly soluble with the extension of peptide chain, so that a large amount of solvent is required for the synthesis reaction of a protein. However, the use of a large amount of solvent causes the reactivity of the reactants in the intended reaction to be lowered. When the reaction is carried out under drastic conditions in order to avoid lowering of the reactivity, racemization and/or other side reactions tend to occur to a large extent so that it becomes difficult to obtain the intended product. On the other hand, in the solid phase method, the above problems are not involved. However, in the solid phase method, proteins are synthesized through many steps of reactions so that defective peptides formed due to incomplete reactions accumulate. In such case, it is difficult to remove the accumulated defective peptides at the final purification step. In either method, a long time is required to synthesize proteins because the synthesis of protein is performed by bonding necessary amino acids one by one.

As is apparent from the above, it is difficult to synthesize proteins completely artificially. So, as a more convenient method of the synthesis of proteins, there was proposed a semisynthetic method in which a peptide fragment of the kind which can be easily synthesized is first synthesized, and then mixed with or linked to a natural protein fragment extracted, through the partial decomposition of the natural protein, from the living body to obtain a protein having a physiological activity [K. Hofmann, Journal of American Chemical Society, 88, 4107 (1966)] [(A. Komoriya et al., International Journal of Peptide and Protein Research, 166, 433 (1980)]. However, this method does not have any industrial value, because the proteins obtained in this method are not those which have been newly provided but those which have been obtained by partially decomposing natural proteins, followed by reconstruction through semisynthesis. As another semisynthetic method, although it is restricted to a special case, there was proposed a method in which a synthetic octapeptide is bonded to swine insulin fragments by means of an enzyme to obtain human insulin [K. Inouye et al., Journal of the American Chemical Society, 101, 751 (1979)]. This enzymatic method which is useful in synthesis of human insulin was reported in M. Bergmann and H. Francel Conrat, Journal of Biological Chemistry, vol. 124, p. 1 (1983). Recently, the usefulness of the enzymatic method was re-confirmed. In this respect, reference may be made to Japanese Patent Application Laid-Open Specification No. 51-110094/1976; Japanese Patent Application Laid-Open Specification No. 53-62896/1978; Y. Isowa et al, Bulletin of Chemical Society of Japan, vol. 50, pp. 2762 and 2766 (1977); K. Morihara and T. Oka, Biochemical Journal. vol. 162, p. 531 (1977); R. W. Sealock and M. Laskowski, Biochemistry, vol. 8, p. 3703 (1969); and G. A. Homandberg et al, ibid., vol. 17, p. 5220 (1978). It is to be noted, however, that while the enzymatic method is useful where the difference between the desired peptide of an organism and an available corresponding peptide of another organism resides in the kind of a single amino acid residue only, the method is not generally applicable to the synthesis of a protein since differences with respect to a plurality of amino acid residues exist between the desired protein and an available protein. Moreover, apart from the applicability of the enzymatic method, the use of natural protein fragments obtained by extraction as the raw material is disadvantageous from the viewpoints of availability, purity, danger of contamination with viruses and the like.

According to the progress of recombinant DNA technique, the syntheses of various active peptides using synthetic or natural DNA have been reported following the pioneering work by Goeddel and Itakura [see D. V. Goeddel and K. Itakura: Proceeding National Academy of Science in U.S.A., Vol. 76, p. 106 (1979)]. The syntheses of active peptides by recombinant DNA technique, however, are accompanied by the following drawbacks. First, a large amount of microorganisms or cells which serve to produce active peptides are propagated during the production of active peptides, and it is necessary to dispose of the propagated microorganisms or cells. For the purpose of safety, it is requisite that before the disposal, all of such propagated microorganisms or cells be killed. However, it is very difficult to accomplish this on a commercial scale. Secondly, since the initiation codon for peptide synthesis is identical with the codon of a methionine residue, a peptide directly synthesized by recombinant DNA technique inevitably has a methionine residue at the N-terminus thereof even if the corresponding natural peptide which is desired to be obtained does not have a methionine residue at the N-terminus thereof. Hence, a synthetic peptide obtained by this method cannot be identical with the desired natural peptide with respect to the amino acid residue at the N-terminus.

As an improved method for the synthesis of a physiologically active peptide by recombinant DNA technique, there has heretobefore been proposed a method in which a precursor having the cleaving site at a position of an arginine residue, lysine residue or methionine residue is synthesized by recombinant DNA technique, and the so-synthesized precursor is cleaved by treating it with trypsin, chymotrypsin or cyanogen bromide in accordance with the known method described in G. R. Stark et al., Journal of Biological Chemistry, vol. 235, p. 3177 (1960), and in E. Gross and B. Witkop, Journal of Biological Chemistry, vol. 237, p. 1856 (1962), thereby to obtain a physiologically active peptide (Japanese Patent Application Laid-Open Specification No. 54-145289/1979). The above-mentioned improved method, however, has the following two defects. One of such defects is that in the above-mentioned method, peptide fragments produced by cleavage of the precursor include not only the intended peptides but also undesirable peptide fragments, because the precursor comprises the intended peptide and a peptide fragment attached to the N-terminus of the intended peptide. Another defect is that application of the above-mentioned method is restricted only to the synthesis of an active peptide which does not contain an arginine residue, lysine residue or methionine residue, because if the intended peptide contains an arginine residue, lysine residue or methionine residue, the intended peptide is cut into pieces simultaneously with the desired cleavage. Therefore, this method cannot apply to the synthesis of peptides comprised of a large number of amino acids, such as proteins, since such peptides generally contain an arginine residue, lysine residue or methionine residue.

As another method in which artificial cleavage is involved, there is known a method in which a precursor having an innate cleaving site is produced in a cultured cell of a higher animal, and the so-produced precursor is caused to be cleaved in said cell at the innate cleaving site thereof, thereby to obtain an active peptide [P. W. Gray et al, Nature, vol. 195, p. 503 (1982); R. Devos et al, Nucleic Acid Research, vol. 10, p. 2487 (1982); Japanese Patent Application Laid-Open Specification No. 58-90514/1983; and T. Taniguchi et al, Nature, vol. 302, p. 305 (1983)]. According to this method, an active protein not having methionine at the N-terminus thereof can be synthesized, but the productivity is extremely low and, hence, this method cannot apply to the industrial-scale synthesis of an active peptide.

As an improvement of the above-mentioned method in which a precursor is produced in a cultured cell, there is known a method in which a precursor having an innate cleaving site is produced using, in place of a cultured cell of a higher animal, a yeast which is a eucaryotic cell of a microorganism, and the so-produced precursor is cleaved in said yeast at the innate cleaving site thereof, thereby to obtain an active peptide [R. A. Hitzeman et al, Science, vol. 219, p. 520 (1983)]. However, in this method, the yeast serves to cleave the precursor at the innate cleaving site thereof, but it also cleaves the precursor at a site other than the innate cleaving site and, hence, if the synthesis of an active peptide is effected by using this method, there is produced a mixture of peptides which are different in length. In the case of the above-mentioned method in which a precursor is cleaved in the yeast, there is such a disadvantage that active peptide-producing yeasts are caused to be produced in large quantities. Therefore, when the synthesis of an active peptide is effected by this method, it is requisite that, for the purpose of safety, all of such peptide-producing yeasts be killed.

On the other hand, as a method for removing only the methionine residue attached to the N-terminus of the intended peptide produced by recombinant DNA technique while leaving other methionine residues, if any, in the intended peptide as they are, the present inventor established a method of removing only the methionine residue attached to the N-terminus of the peptide by the so-called phenylisothiocyanate method or the so-called aminopeptidase method (Japanese Patent Application Laid-Open Specification No. 58-110548/1983). The phenylisothiocyanate method is disclosed in P. Edman, Acta Chemica Scandinavia, 4, 227, (1950) and the aminopeptidase method is disclosed in D. H. Spackman et al, Journal of Biological Chemistry, 212, 255 (1955) and E. D. Wacksmuth, Biochemistry, 5, 169 and 175 (1966). However, this method has a disadvantage that not only the intended peptide is denatured but also other amino acid residues in the amino acid sequence of the peptide as well as the methionine residue attached to the N-terminus of the intended peptide are removed successively from the N-terminus of the intended peptide.

In summary, conventionally, when a protein composed of amino acid residues as many as about 50 or more is intended to be produced by organic synthesis, there is a disadvantage in that many complicated reaction steps are needed and a long period of time is required to produce peptides. Further, when the amino acid residues to be linked have low reactivity, even if they are reacted the reaction yield is low and it is necessary to isolate the desired product from the raw materials remaining unreacted in the reaction step. Moreover, as mentioned above, when a protein composed of amino acid residues as many as about 50 or more is intended, the synthesis method inevitably involves many complicated steps of reactions, leading to occurrence of side reactions in each step. As a result, the yield of the intended product is lowered and it is necessary to isolate the intended product from a large amount of the by-products. The isolation is very difficult to perform.

On the other hand, when a protein having a large molecular weight is intended to be produced directly by recominant DNA technique with respect to the entire amino acid sequence of the protein, the peptide which contains at least one methionine residue in its amino acid sequence but does not have a methionine residue as the N-terminal amino acid residue cannot be produced. This is because a product prepared by recombinant DNA technique inevitably has a methionine residue as the N-terminal amino acid residue for the reason as set forth before and, as mentioned above, the selective removal of only such a methionine residue attached to the N-terminus of the intended protein is extremely difficult. Further, it is dangerous if the microorganisms or cells used in the culturing step for producing the intended protein are released out of the culture system and, therefore, it is necessary to kill all of the used microorganisms or cells in the culture system after culturing. However, it is difficult to kill all of the microorganisms or cells on an industrial scale.

The present inventor has made extensive and intensive studies in order to overcome the above-mentioned defects of the conventional methods. As a result, the present inventor has found that the intended active protein can be easily and safely produced by providing two peptide fragments, at least one of which is one which has been obtained by recombinant DNA technique or has been obtained by a method comprising preparing a predetermined peptide fragment by recombinant DNA technique and deleting from or adding to said predetermind peptide fragment at its N-terminus at least one amino acid residue, and linking said two peptide fragments to each other. The present invention has been made based on such a novel finding.

Therefore, it is a primary object of the present invention to provide a novel method for easily and safely producing an active protein on an industrial scale.

SUMMARY OF THE INVENTION

According to the present invention, there is provided a method for producing an active protein which comprises:

(1) providing:

(a) a first peptide fragment having a first amino acid sequence corresponding to part of an active protein, said first amino acid sequence containing the N-terminal amino acid residue of the active protein, and (b) a second peptide fragment having a second amino acid sequence corresponding to the remaining part of the active protein, said second amino acid sequence containing the C-terminal amino acid residue of the active protein, at least one of said first peptide fragment and said second peptide fragment being one which has been obtained by recombinant DNA technique or has been obtained by a method comprising producing a predetermined peptide fragment by recombinant DNA technique and deleting from or adding to said predetermined peptide fragment at its N-terminus at least one amino acid residue; and (2) linking said first peptide fragment at its C-terminus to said second peptide fragment at its N-terminus.

In practicing the method of the present invention, a first peptide fragment and a second peptide fragment are provided. The first peptide fragment has a first amino acid sequence corresponding to part of a desired active protein, said first amino acid sequence containing the N-terminal amino acid residue of the active protein. The second peptide fragment has a second amino acid sequence corresponding to the remaining part of the active protein, said second amino acid sequence containing the C-terminal amino acid residue of the active protein. The above-mentioned first peptide fragment and the above-mentioned second peptide fragment are hereinafter often referred to as "material N" and "material C", respectively.

According to the method of the present invention, at least one of the material N and the material C must be one which has been obtained by recombinant DNA technique or has been obtained by a method comprising producing a predetermined peptide fragment by recombinant DNA technique and deleting from or adding to said predetermined peptide fragment at its N-terminus at least one amino acid residue.

The amino acid sequence of the material N and the amino acid sequence of the material C may generally be predetermined so that the C-terminal amino acid residue of the material N may be reactive with the N-terminal amino acid residue of the material C and so that the C-terminal amino acid residue of the material N and the N-terminal amino acid residue of the material C may not cause side reactions such as racemization. Actually, the above-mentioned predetermination is effected by appropriate choice of a combination of amino acid residues to be reacted with each other, taking into consideration the kinds of amino acid residues in the amino sequence of the intended protein.

Where the desired active protein has at least one methionine residue in its amino acid sequence at an intermediate portion between the N-terminal amino acid residue and the C-terminal amino acid residue of the active protein, it is advantageous to predetermine the amino acid sequence of the material N and the amino acid sequence of the material C so that a first occurring methionine residue subsequent to the N-terminal amino acid residue of the active protein constitutes the N-terminal amino acid residue of the amino acid sequence of the material C. The reasons for this are as follows. With respect to the material N, if the amino acid sequence of the desired protein has a methionine residue as the N-terminal amino acid residue, a peptide fragment corresponding to the amino acid sequence of a predetermined material N can be easily prepared directly by recombinant DNA technique and, as such, can be employed as a material N, since the N-terminal amino acid residue of the material N is identical with the amino acid residue produced from the initiation codon for translating from mRNA to a peptide in the recombinant DNA technique. Even if the N-terminal amino acid residue of the desired protein is not a methionine residue, a peptide fragment corresponding to the amino acid, sequence of a predetermined material N can be easily obtained by a method in which a predetermined peptide fragment comprising a peptide fragment corresponding to the amino acid sequence of a predetermined material N and a methionine residue attached to the N-terminus of the peptide fragment is first prepared by recombinant DNA technique and the methionine residue is then deleted from the predetermined peptide fragment at its N-terminus. The deletion of the methionine residue attached to the N-terminus of the predetermined peptide fragment can be easily performed by means of cyanogen bromide without causing the material N to be cut into pieces because the material N contains no methionine residue in the amino acid sequence. On the other hand, a peptide fragment corresponding to the amino acid sequence of a predetermined material C can be easily prepared directly by recombinant DNA technique and, as such, can be employed as a material C because the material C is usually constructed to have a methionine residue at the N-terminus of the amino acid sequence.

If the reactivity of the C-terminal amino acid residue of the predetermined material N for the N-terminal amino acid residue, i.e., usually a methionine residue, of the material C is poor, or if the reaction between the C-terminal amino acid residue of the material N and the N-terminal amino acid residue of the material C is accompanied by undesirable side reactions, the amino acid sequence of the material N and the amino acid sequence of the material C may preferably be predetermined so that an amino acid residue positioned near the first occurring methionine residue subsequent to the N-terminal amino acid residue of the desired protein on the side of the N-terminus of the desired protein constitutes the N-terminal amino acid residue of the material C and so that the C-terminal amino acid of the material N has high reactivity with the N-terminal acid of the material C. In this case, with respect to the material N, a peptide fragment corresponding to the amino acid sequence of the predetermined material N can be easily prepared using recombinant DNA technique in the same manner as mentioned above. On the other hand, with respect to the material C, a peptide fragment corresponding to the amino acid sequence of a predetermined material C can also be easily prepared using recombinant DNA technique. That is, a predetermined peptide fragment of which the N-terminal amino acid residue is the above-mentioned first occurring methionine residue subsequent to the N-terminal amino acid residue of the desired active protein is first prepared by recombinant DNA technique and at least one amino acid residue is then added to the N-terminus of the above-prepared peptide fragment by organic synthesis. When a plurality of amino acid residues are to be added there may advantageously be employed an oligopeptide residue.

Where the intended active protein contains no methionine residues not only at the intermediate portion but also at the N-terminus of the amino acid sequence thereof, a peptide fragment corresponding to the amino acid sequence of a predetermined material N and/or a peptide fragment corresponding to the amino acid sequence of a predetermined material C can be easily obtained using recombinant DNA technique. With respect to the material N, a peptide fragment corresponding to the amino acid sequence of a predetermined material N can be easily obtained by a method in which a predetermined peptide fragment comprising a peptide fragment corresponding to the amino acid sequence of a predetermined material N and a methionine residue attached to the N-terminus of the peptide fragment is first prepared by recombinant DNA technique and the methionine residue attached to the N-terminus of the predetermined peptide fragment is then deleted. With respect to the material C, a peptide fragment corresponding to the amino acid sequence of a predetermined material C can be easily obtained in substantially the same manner as mentioned above.

As mentioned above, the desired active protein is easily, safely produced by a method in which (1) the amino acid sequence for the material N and the amino acid sequence for the material C are skillfully predetermined, (2) at least one of the material N and the material C is prepared by recombinant DNA technique or producing a predetermined peptide fragment by recombinant DNA technique and deleting from or adding to said predetermined peptide fragment at its N-terminus at least one amino acid residue, and (3) the material N is linked, at its C-terminus, to the material C at its N-terminus.

When, for example, either a peptide fragment corresponding to the amino acid sequence of the predetermined material N or a peptide fragment corresponding to the amino acid sequence of the predetermined material C is short in length and can be easily prepared by organic synthesis, or can be easily obtained from a natural source, such as peptide fragment may be used as a material to be linked with another material prepared using recombinant DNA technique.

The linking of the material N at its C-terminus to the material C at its N-terminus may be effected according to customary methods, for example, the method as described in Nobuo Izumiya et al, "synthetic chemistry series-syntheses of peptides" published by Maruzen K.K., Japan, 1975. Illustratively stated, the material N may be reacted with the material C in the presence of a condensation agent to link the C-terminus of the material N to the N-terminus of the material C through a peptide linkage.

As the condensation agent, there may be employed, for example, chemical condensation agents and proteases. As suitable examples of the chemical condensation agents, there may be mentioned well-known chemical condensation agents used for linking an acid component and an amine component, such as N,N'-dicyclohexylcarbodiimide (hereinafter referred to as "DCC"), 1-ethoxycarbonyl-2-ethoxy-1,2-dihydroquinoline (hereinafter referred to as "EEDQ"), the Woodward's agent K and 2,2-dipyridyldisulfide.

As the protease, there may be employed well-known enzymes which hydrolyze proteins such as an enzyme which is capable of cleaving a peptide linkage present on the carboxyl group side of a substrate amino acid residue (hereinafter referred to as "enzyme C"), an enzyme which is capable of cleaving a peptide linkage present on the amino group side of a substrate amino acid residue (hereinafter referred to as "enzyme N"), an enzyme which is capable of cleaving a peptide linkage present between the adjoining two substrate amino acid residues (hereinafter referred to as "enzyme M").

As suitable examples of the enzyme C, there may be mentioned well-known enzymes used for determining an amino acid sequence, for example, trypsin (substrate amino acid residue: a lysin residue and an arginine residue), chymotrypsin (substrate amino acid residue: aromatic amino acid residues), staphylococcal protease (substrate amino acid residue: a glutamic acid residue and an aspartic acid residue) [J. Houmard and G. R. Drapeau, Proceeding National Academy of Science in U.S.A., 69, 3506 (1972)], mouse submaxillary proteases A and D (substrate amino acid residue: an arginine residue) [M. Boeman et al., Arch, Biochem. Biophys., 175, 463 (1976)], post-proline cleaving enzyme (substrate amino acid residue: a proline residue) [M. Koida and R. Walter, Journal of Biological Chemistry, 251, 7593 (1976)], proline specific endopeptidase (substrate amino acid residue: a proline residue) [T. Yoshimoto and D. Tsuru, Agricultural and Biological Chemistry, 42, 3017 (1978)], achromobacter proteases I (substrate amino acid residue: a lysin residue) [T. Masaki et al., ibid. 42, 1443 (1978)], endoproteinase lys-C (Japanese Patent Application Laid-Open Specification No. 57-49884/1982), pepsin, and the like.

As suitable examples of the enzyme N, there may be mentioned well-known enzymes also used for determining an amino acid sequence, for example, thermolysin, myxobacter AL-I protease II (substrate amino acid residue: a lysin residue) [M. Wingard et al., Journal Bacteriology, 112, 940 (1972)], Armillaria mella protease (substrate amino acid residue: a lysin residue) [G. W. Lewis et al., Biochem. Biophys. Acta. 522, 551 (1978)], and the like.

As the enzyme M, there may be mentioned, for example, well-known enzymes which are capable of cleaving a natural precursor peptide to produce a mature peptide.

Alternatively, the material N may be linked to the material C as follows. Either the material N or the material C is reacted with a suitable activating agent to convert the material to an activated form having a reactive group (hereinafter often referred to as "activated derivative"). In the case of the material N, the C-terminus of the material is reacted with an activating agent to form a corresponding activated derivative, whereas in the case of the material C, the N-terminus of the material is reacted with an activating agent to form a corresponding activated derivative. Subsequently, the reaction for linking the material N to the material C is effected. In this instance, due to the high reactivity of the terminus of the material, the reaction proceeds smoothly in the absence of any agent such as the above-mentioned condensation agent.

As the reactive group of the activated derivative, there may be mentioned groups well-known in the art as a reactive group for forming a peptide linkage such as an azido group and a reactive ester group.

Of the above-mentioned methods of linking the material N to the material C, preference will be explained as follows. From a viewpoint of prevention of racemization, the use of an activated derivative of the material N is more preferable than that of material C.

The use of a chemical condensation agent is more preferable than the use of an activated derivative of the material N except for an azido group-activated derivative. The use of the azido group-activated derivative of the material N is more preferable than the use of a chemical condensation agent. Further, the use of a protease is more preferable than the use of the azido group-activated derivative of the material N. However, the above-mentioned estimation of preference of the linking method varies according to the amino acid sequence of the material N and the material C. For example, as the condensation agent, there may be preferably employed DCC, trypsin, chymotrypsin and pepsin, respectively in the cases where the C-terminal amino acid residue of the material N is a proline residue, where it is an arginine residue or lysin residue, where it is a tyrosine residue, phenylalanine residue or tryptophan residue, and where it is a leucine residue, alanine residue, glutamic acid residue, crystine residue or cysteine residue. Further, as the condensation agent, there may be preferably employed thermolysin where the N-terminal amino acid residue of the material C is an isoleucine residue, leucine residue, valine residue, phenylalanine residue, methionine residue or alanine residue. Moreover, where the material N is one prepared by organic synthesis, an azido group-activated derivative of the material N is preferably employed. If the amino acid sequence of the material N and the amino acid sequence of the material C are skillfully predetermined so that a first occurring methionine residue subsequent to the N-terminal amino acid residue of the active protein constitutes the N-terminal amino acid residue of the amino acid sequence of the material C, as described before, at least one of the material N and the material C can be easily obtained using recombinant DNA technique. When a peptide fragment corresponding to the amino acid sequence of the predetermined material C is prepared by recombinant DNA technique, the peptide fragment obtained has a methionine residue attached to the N-terminus of the peptide fragment. In such a case, using an enzyme N specific to a methionine residue, the material N is easily linked, at its C-terminus, to the material C at its N-terminus to produce the desired protein.

In conducting the reaction for linking the material N to the material C, the functional groups of the material N and the material C except the C-terminus of the material N and the N-terminus of the material C may, according to need, be protected by protecting groups.

The functional groups to be protected in the present invention are generally those cited below, but not limited thereto. For example, when a chemical condensation agent is employed for linking the material N to the material C, the functional groups to be protected are the N-terminus of the material N, the C-terminus of the material C and the pendant functional groups of both of the materials. When the enzyme C is employed, the N-terminus of the material N and the pendant amino groups, except the C-terminus of the material N, hydroxyl groups and SH groups of both of the materials may be protected. The C-terminus of the material C is protected in the event that it is that of a substrate amino acid. When the enzyme N is employed, the N-terminus of the material N is protected in the event that it is that of a substrate amino acid. Further, it may be preferable to protect the C-terminus of the material C and the pendant carboxyl groups, except the N-terminus of the material C, of both of the materials. When an azido group-activated derivative is employed, the N-terminus of the material N and the pendant amino groups and SH groups of both of the material are protected. When an activated derivative other than an azido group-activated derivative is employed, the N-terminus of the material N, the C-terminus of the material C and the pendant functional groups of both of the materials are protected.

As the protecting group to be employed to protect the N-terminus, there may be mentioned any groups generally known in the art as the N-terminus protecting group, for example, a carbobenzoxy group (hereinafter referred to as "Z group"), a substituted carbobenzoxy group such as p-methoxybenzyloxycarbonyl group (hereinafter referred to as "pMZ group"), a t-butoxycarbonyl group (hereinafter referred to as "Boc group"), a tosyl group (hereinafter referred to as "Tos group") and the like. As the protecting group to be employed to protect the C-terminus, there may be mentioned any groups generally known in the art as the C-terminus protecting group, for example, a methyl ester group, an ethyl ester group, a benzyl ester group, a t-butyl ester group, a p-nitrobenzyl ester group and the like. As the protecting group to be employed to protect the pendant functional groups of the materials, there may be mentioned any groups generally known in the art as the pendant group protecting group. For example, as the ω-amino protecting group, there may be mentioned a Z group, a Boc group and the like. As the guanidino(G) protecting group, there may be mentioned a G-nitro group, a G-Tos group, a G-Z group and the like. As the imidazolyl protecting group, there may be mentioned an im-benzyl(im) group, an im-Z group, an im-Tos group and the like.

As the ω-carboxyl protecting group, there may be mentioned a methyl ester group, an ethyl ester group, a benzyl ester group, a t-butyl ester group, a p-nitrobenzyl ester group and the like. As the ω-carbamide protecting group, there may be mentioned a γ-xanthyl group, a bis-2,4-dimethoxybenzyl group [hereinafter referred to as "$(DMB)_2$ group"] and the like. As the hydroxyl protecting group, there may be mentioned a benzyl group (hereinafter referred to as "Bzl group"), a tertiary butyl group (hereinafter referred to as "t-Bu group") and the like. As the mercapto protecting group, there may be mentioned a Bzl group, a p-methoxybenzyl group (hereinafter referred to a "Bzl (OMe) group") and the like.

Any solvents generally known in the art as the solvent being useful for syntheses of proteins may be used as the reaction solvent in performing the method of the present invention. Specific examples of such solvents are dimethylformamide (hereinafter referred to as "DMF"), dimethylsulfoxide (hereinafter referred to as "DMSO"), hexamethylene phosphamide (hereinafter referred to as "HMPA"), N-methylpyrrolidone (hereinafter referred to as "NMP"), diethyl phosphite, trifluoroethanol, hexafluoroisopropanol and the like. When a protease is used as the condensation agent, it may be preferable to employ a mixed solvent composed of a solvent selected from the above solvents and a buffer solution. The pH value of such a mixed solvent may be adjusted to a value at which the above-mentioned enzyme exhibits activity. For example, when the employed protease is a member selected from the group consisting of trypsin, chymotrypsin, thermolysin, staphylococcal protease, myxobacter-AL-I protease II, Armillaria mella protease, mouse submaxillary proteases A and D, post-proline cleaving enzyme, proline specific endopeptidase, achromobacter protease I, endoproteinanse lys-C and the like, the pH value of such a mixed solvent may be in the range of generally from 4 to 10, preferably from 7 to 9. Meanwhile, when the employed protease is pepsin, the pH value of such a mixed solvent may be in the range of generally from 2 to 6, preferably from 3 to 5.

In the method of the present invention, the molar ratio of the condensation agent of each of the charged materials is not critical. Generally, a sufficient amount of the condensation agent may be from 0.9 to 2 moles in the case of a chemical condensation agent and from 0.1 to 10 millimoles in the case of a protease per mole of material N or material C, which is larger in amount. The material N and material C may be charged in equimolar amounts. According to need, however, the charged amount of either of the materials N and C may exceed that of the other. For example, the molar ratio of the material N to the material C may be in the range of generally from 1:5 to 5:1, preferably from 1:2 to 2:1. The condensation reaction may be effected at a temperature as set forth below over a period of time as set forth below. The suitably employable temperature and period of time are, however, not limited thereto. Generally, in the case of use of the above-mentioned chemical condensation agent or activation derivative, the condensation reaction may be performed at a temperature of from −20° to 0° C. over a period of from 20 to 40 hours. In the case of a thermostable enzyme such as thermolysin or the like, the condensation reaction may be performed at a temperature of from 0° to 80° C., preferably from 30° to 60° C., over a period from 1 to 20 hours. In the case of a non-thermostable enzyme such as trypsin, chymotrypsin, pepsin, staphylococcal protease, myxobacter-AL-I protease II, Armillaria mella protease, mouse submaxillary proteases A and D, post-proline cleaving enzyme, proline specific endopeptidase, achromobacter protease I, endoproteinase lys-C or the like, the condensation reaction may be performed at a temperature of from 20° C. to 50° C., preferably from 30° C. to 40° C., over a period of from 1 to 20 hours. The condensation reaction very readily proceeds in the above-mentioned aqueous solvent, and the reaction product may separate out from the solution in the form of crystals due to its sparing solubility in the aqueous solvent. When the reaction product does not separate out in this manner, 1 to 10 volumes of water may be added to the solution to separate the reaction product out in the form of crystals. The resulting crystals may be filtered off and washed with a weakly alkaline aqueous solution, a weakly acidic aqueous solution and water according to customary procedures to obtain a desired product having high purity. The protecting groups of the resulting product may be removed, if desired, according to customary procedures (Nobuo Izumiya et al, "synthetic chemistry series-syntheses of peptides" published by Maruzen K.K., Japan, 1975, pp. 221-).

The method of the present invention may be employed for producing any active proteins. In general, the specific portions of proteins of viruses or microorganisms and proteins of higher animals are composed of 130 or more of non-racemized amino acids. Each of them does not have as the N-terminal amino acid residue a methionine residue but contains at least one methionine residue in the intermediate portion of the amino acid sequence. Such a protein can hardly be produced by the conventional methods, because the protein is too large for the production by organic synthesis and because if the protein is intended to be produced by recombinant DNA technique, the deletion of the N-terminal methionine residue by means of cyanogen bromide is inevitably accompanied by cutting of the amino acid sequence of the protein into pieces. According to the method of the present invention, as described above, such proteins can be easily produced. As examples of the useful specific portions of the proteins of viruses and microorganisms, there may be mentioned B-type heptatitis virus antigenic protein, influenza virus antigenic protein, cancer virus antigenic protein, bovine foot-and-mouth disease virus antigenic protein, cholera vibrio antigenic protein and the like. As the useful higher animal proteins, there may be mentioned, for example, human and bovine growth hormones, human and bovine α-interferons, human and bovine γ-interferons, human interleukin-1, human interleukin-2, human urokinase, human tissue plasminogen activator, human hemoglobin α chain, human hemoglobin β chain, human prorelaxin, human albumin, human macrophage migration inhibitory factor MIF, cytotoxic factor TCLF, CBF, CSF, and the like.

As preferred embodiments of the present invention, there may be mentioned: a process for producing human interferon-γ (hereinafter referred to as "IFN-γ") which comprises effecting a condensation in the presence of trypsin between a peptide [hereinafter referred to as "IFN-γ-(1–46)"] having the same amino acid sequence as that of from the N-terminal amino acid residue to the 46-th amino acid residue of IFN-γ and a peptide [hereinafter referred to as "IFN-γ-(47–146)"] having the same amino acid sequence as that of from the 47-th amino acid residue to the C-terminal amino acid residue of IFN-γ; a process for producing human interleukin-2 (hereinafter referred to as "IL-2") which comprises effecting a condensation in the presence of pepsin between a peptide [hereinafter referred to as "IL-2-(1–22)"] having the same amino acid sequence as that of from the N-terminal amino acid residue to the 22-nd amino acid residue of IL-2, with its N-terminus, pendant amino groups, pendant hydroxyl groups and pendant SH groups being protected by protecting groups, and a peptide [hereinafter referred to as "IL-2-(23–133)"] having the same amino acid sequence as that of from the 23-rd amino acid residue to the C-terminal amino acid residue of IL-2, with its pendant amino groups, pendant hydroxyl groups and pendant SH groups being protected by protecting groups, and subsequently removing the protecting groups; a process for producing human tissue plasminogen activator (hereinafter referred to as "TPA") which comprises effecting a condensation between an azido group-activated derivative of a peptide [hereinafter referred to as "TPA-(1–12)"] having the same amino acid sequence as that of from the N-terminal amino acid residue to the 12-th amino acid residue of TPA, which its N-terminus, pendant amino groups, pendant hydroxyl groups and pendant SH groups being protected by protecting groups, and a peptide [hereinafter referred to as "TPA-(13–527)] having the same amino acid as that of from the 13-th amino acid residue to the C-terminal amino acid residue of TPA, with its pendant amino groups, pendant hydroxyl groups and pendant SH groups being protected by protecting groups, and subsequently removing the protecting groups; a process for producing human prorelaxin (hereinafter referred to as "ProLXN") which comprises effecting a condensation in the presence of DCC between a peptide [hereinafter referred to as "Pro LXN-(1–23)"] having the same amino acid sequence as that of from the N-terminal amino acid residue to the 23-rd amino acid residue of ProLXN, with its N-terminus and pendant functional groups being protected by protecting groups, and a peptide [hereinafter referred to as "ProLXN-(24–160)"] having the same amino acid sequence as that of from the 24-th amino acid residue to the C-terminal amino acid residue of ProLXN, with its C-terminus and pendant functional groups being protected by protecting groups, and subsequently removing the protecting groups; a process for producing human hemoglobin α chain (hereinafter referred to as "Hb-α") which comprises effecting a condensation in the presence of thermolysin between a peptide [hereinafter referred to as "Hb-α-(1–31)"] having the same amino acid sequence as that of from the N-terminal amino acid residue to the 31-st amino acid residue of Hb-α and a peptide [hereinafter referred to as "Hb-α-(32–141)"] having the same amino acid sequence as that of from the 32-nd amino acid to the C-terminal amino acid residue of Hb-α, with its C-terminus being protected by a protecting group; a process for producing Hb-α which comprises a condensation in the presence of trypsin between Hb-α-(1–31) having the N-terminus protected by a protecting group and Hb-α-(32–160) having the C-terminus protected by a protecting group; and the like.

The amino acid sequences of the raw materials to be employed and products to be obtained in the above-mentioned specific embodiments of the present invention are as follows.

In the following, amino acids and peptides are represented using abbreviations, as indicated below, approved by IUPAC-IUB Commission on Biochemical Nomenclature (CBN). Incidentally, with respect to amino acids and the like having isomers, those represented by the following abbreviations are of the L-configuration unless otherwise specified.

Gln: glutamine residue
Asp: aspartic acid residue
Pro: proline residue
Tyr: tyrosine residue
Val: valine residue
Lys: lysine residue
Glu: glutamic acid residue
Ala: alanine residue
Asn: asparagine residue
Leu: leucine residue
Phe: phenylalanine residue
Gly: glycine residue
His: histidine residue
Ser: serine residue
Thr: threonine residue
Ile: isoleucine residue
Trp: tryptophan residue
Arg: arginine residue
Met: methionine residue
Cys: cysteine residue Amino Acid Sequence of IFN-γ-(1–46): Cys Tyr Cys Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Try Lys Glu Glu Ser Asp Arg Lys.

Amino Acid Sequence of IFN-γ-(47–146): Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln.

Amino Acid Sequence of IFN-γ: Cys Tyr Cys Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln.

Amino Acid Sequence of IL-2-(1–22): Ala Pro Thr Ser Ser Ser Thr Lys Lys Thr Gln Leu Gln Leu Glu His Leu Leu Leu Asp Leu Gln.

Amino Acid Sequence of IL-2-(23–133): Met Ile Leu Asn Gly Ile Asn Asn Tyr Lys Asn Pro Lys Leu Thr Arg Met Leu Thr Phe Lys Phe Tyr Met Pro Lys Lys Ala Thr Glu Leu Lys His Leu Gln Cys Leu Glu Glu Glu Leu Lys Pro Leu Gln Glu Val Leu Asn Leu Ala Gln Ser Lys Asn Phe His Leu Arg Pro Arg Asp Leu Ile Ser Asn Ile Asn Val Ile Val Leu Glu Leu Lys Gly Ser Glu Thr Thr Phe Met Cys Glu Tyr Ala Asp Glu Thr Ala Thr Ile Val Glu Phe Leu Asn Arg Trp Ile Thr Phe Cys Gln Ser Ile Ile Ser Thr Leu Thr.

Amino Acid Sequence of IL-2: Ala Pro Thr Ser Ser Ser Thr Lys Lys Thr Gln Leu Gln Leu Glu His Leu Leu Leu Asp Leu Gln Met Ile Leu Asn Gly Ile Asn Asn Tyr Lys Asn Pro Lys Leu Thr Arg Met Leu Thr Phe Lys Phe Tyr Met Pro Lys Lys Ala Thr Glu Leu Lys His Leu Gln Cys Leu Glu Glu Glu Leu Lys Pro Leu Glu Glu Val Leu Asn Leu Ala Gln Ser Lys Asn Phe His Leu Arg Pro Arg Asp Leu Ile Ser Asn Ile Asn Val Ile Val Leu Glu Leu Lys Gly Ser Glu Thr Thr Phe Met Cys Glu Tyr Ala Asp Glu Thr Ala Thr Ile Val Glu Phe Leu Asn Arg Trp Ile Thr Phe Cys Gln Ser Ile Ile Ser Thr Leu Thr.

Amino Acid Sequence of TPA-(1-12) Azide or Its Precursor Hydrazide: Ser Tyr Gln Val Ile Cys Arg Asp Glu Lys Thr Gln $N_3$ (or $NHNH_2$).

Amino Acid Sequence of TPA(13-527): Met Ile Tyr Gln Gln His Gln Ser Trp Leu Arg Pro Val Leu Arg Ser Asn Arg Val Glu Tyr Cys Trp Cys Asn Ser Gly Arg Ala Gln Cys His Ser Val Pro Val Lys Ser Cys Ser Glu Pro Arg Cys Phe Asn Gly Gly Thr Cys Gln Gln Ala Leu Tyr Phe Ser Asp Phe Val Cys Gln Cys Pro Glu Gly Phe Ala Gly Lys Cys Cys Glu Ile Asp Thr Arg Ala Thr Cys Tyr Glu Asp Gln Gly Ile Ser Tyr Arg Gly Thr Trp Ser Thr Ala Glu Ser Gly Ala Glu Cys Thr Asn Trp Asn Ser Ser Ala Leu Ala Gln Lys Pro Tyr Ser Gly Arg Arg Pro Asp Ala Ile Arg Leu Gly Leu Gly Asn His Asn Tyr Cys Arg Asn Pro Asp Arg Asp Ser Lys Pro Trp Cys Tyr Val Phe Lys Ala Gly Lys Tyr Ser Ser Glu Phe Cys Ser Thr Pro Ala Cys Ser Glu Gly Asn Ser Asp Cys Tyr Phe Gly Asn Gly Ser Ala Tyr Arg Gly Thr His Ser Leu Thr Glu Ser Gly Ala Ser Cys Leu Pro Trp Asn Ser Met Ile Leu Ile Gly Lys Val Tyr Thr Ala Gln Asn Pro Ser Ala Gln Ala Leu Gly Leu Gly Lys His Asn Tyr Cys Arg Asn Pro Asp Gly Asp Ala Lys Pro Trp Cys His Val Leu Lys Asn Arg Arg Leu Thr Trp Glu Tyr Cys Asp Val Pro Ser Cys Ser Thr Cys Gly Leu Arg Gln Tyr Ser Gln Pro Gln Phe Arg Ile Lys Gly Gly Leu Phe Ala Asp Ile Ala Ser His Pro Trp Gln Ala Ala Ile Phe Ala Lys His Arg Arg Ser Pro Gly Glu Arg Phe Leu Cys Gly Gly Ile Leu Ile Ser Ser Cys Trp Ile Leu Ser Ala Ala His Cys Phe Gln Glu Arg Phe Pro Pro His His Leu Thr Val Ile Leu Gly Arg Thr Tyr Arg Val Val Pro Gly Glu Glu Glu Gln Lys Phe Glu Val Glu Lys Tyr Ile Val His Lys Glu Phe Asp Asp Asp Thr Tyr Asp Asn Asp Ile Ala Leu Leu Gln Leu Lys Ser Asp Ser Ser Arg Cys Ala Gln Glu Ser Ser Val Val Arg Thr Val Cys Leu Pro Pro Ala Asp Leu Gln Leu Pro Asp Trp Thr Glu Cys Glu Leu Ser Gly Tyr Gly Lys His Glu Ala Leu Ser Pro Phe Tyr Ser Glu Arg Leu Lys Glu Ala His Val Arg Leu Tyr Pro Ser Ser Arg Cys Thr Ser Gln His Leu Leu Asn Arg Thr Val Thr Asp Asn Met Leu Cys Ala Gly Asp Thr Arg Ser Gly Gly Pro Gln Ala Asn Leu His Asp Ala Cys Gln Gly Asp Ser Gly Gly Pro Leu Val Cys Leu Asn Asp Gly Arg Met Thr Leu Val Gly Ile Ile Ser Trp Gly Leu Gly Cys Gly Gln Lys Asp Val Pro Gly Val Tyr Thr Lys Val Thr Asn Tyr Leu Asp Trp Ile Arg Asp Asn Met Arg Pro.

Amino Acid Sequence of TPA: Ser Tyr Gln Val Ile Cys Arg Asp Glu Lys Thr Gln Met Ile Tyr Gln Glu His Gln Ser Trp Leu Arg Pro Val Leu Arg Ser Asn Arg Val Glu Tyr Cys Trp Cys Asn Ser Gly Arg Ala Gln Cys His Ser Val Pro Val Lys Ser Cys Ser Glu Pro Arg Cys Phe Asn Gly Gly Thr Cys Gln Gln Ala Leu Tyr Phe Ser Asp Phe Val Cys Gln Cys Pro Glu Gly Phe Ala Gly Lys Cys Cys Glu Ile Asp Thr Arg Ala Thr Cys Tyr Glu Asp Gln Gly Ile Ser Tyr Arg Gly Thr Trp Ser Thr Ala Glu Ser Gly Ala Glu Cys Thr Asn Trp Asn Ser Ser Ala Leu Ala Gln Lys Pro Tyr Ser Gly Arg Arg Pro Asp Ala Ile Arg Leu Gly Leu Gly Asn His Asn Tyr Cys Arg Asn Pro Asp Arg Asp Ser Lys Pro Trp Cys Tyr Val Phe Lys Ala Gly Lys Tyr Ser Ser Glu Phe Cys Ser Thr Pro Ala Cys Ser Glu Gly Asn Ser Asp Cys Tyr Phe Gly Asn Gly Ser Ala Tyr Arg Gly Thr His Ser Leu Thr Glu Ser Gly Ala Ser Cys Leu Pro Trp Asn Ser Met Ile Leu Ile Gly Lys Val Tyr Thr Ala Gln Asn Pro Ser Ala Gln Ala Leu Gly Leu Gly Lys His Asn Tyr Cys Arg Asn Pro Asp Gly Asp Ala Lys Pro Trp Cys His Val Leu Lys Asn Arg Arg Leu Thr Trp Glu Tyr Cys Asp Val Pro Ser Cys Ser Thr Cys Gly Leu Arg Gln Tyr Ser Gln Pro Gln Phe Arg Ile Lys Gly Gly Leu Phe Ala Asp Ile Ala Ser His Pro Trp Gln Ala Ala Ile Phe Ala Lys His Arg Arg Ser Pro Gly Glu Arg Phe Leu Cys Gly Gly Ile Leu Ile Ser Ser Cys Trp Ile Leu Ser Ala Ala His Cys Phe Gln Glu Arg Phe Pro Pro His His Leu Thr Val Ile Leu Gly Arg Thr Tyr Arg Val Val Pro Gly Glu Glu Glu Gln Lys Phe Glu Val Glu Lys Tyr Ile Val His Lys Glu Phe Asp Asp Asp Thr Tyr Asp Asn Asp Ile Ala Leu Leu Gln Leu Lys Ser Asp Ser Ser Arg Cys Ala Gln Glu Ser Ser Val Val Arg Thr Val Cys Leu Pro Pro Ala Asp Leu Gln Leu Pro Asp Trp Thr Glu Cys Glu Leu Ser Gly Tyr Gly Lys His Glu Ala Leu Ser Pro Phe Tyr Ser Glu Arg Leu Lys Glu Ala His Val Arg Leu Tyr Pro Ser Ser Arg Cys Thr Ser Gln His Leu Leu Asn Arg Thr Val Thr Asp Asn Met Leu Cys Ala Gly Asp Thr Arg Ser Gly Gly Pro Gln Ala Asn Leu His Asp Ala Cys Gln Gly Asp Ser Gly Gly Pro Leu Val Cys Leu Asn Asp Gly Arg Met Thr Leu Val Gly Ile Ile Ser Trp Gly Leu Gly Cys Gly Gln Lys Asp Val Pro Gly Val Tyr Thr Lys Val Thr Asn Tyr Leu Asp Trp Ile Arg Asp Asn Met Arg Pro.

Amino Acid Sequence of ProLXN-(1-23): Lys Trp Lys Asp Asp Val Ile Lys Leu Cys Gly Arg Glu Leu Val Arg Ala Gln Ile Ala Ile Cys Gly.

Amino Acid Sequence of ProLXN-(24-160): Met Ser Thr Trp Ser Lys Arg Ser Leu Ser Gln Glu Asp Ala Pro Gln Thr Pro Arg Pro Val Ala Glu Ile Val Pro Ser Phe Ile Asn Lys Asp Thr Glu Thr Ile Ile Ile Met Leu Glu Phe Ile Ala Asn Leu Pro Pro Glu Leu Lys Ala Ala Leu Ser Glu Arg Gln Pro Ser Leu Pro Glu Leu Glu Gln Tyr Val Pro Ala Leu Lys Asp Ser Asn Leu Ser Phe Glu Glu Phe Lys Lys Leu Ile Arg Asn Arg Gln Ser Glu Ala Ala Asp Ser Asn Pro Ser Glu Leu Lys Tyr Leu Gly Leu Asp Thr His Ser Gln Lys Lys Arg Arg Pro Tyr Val Ala Leu Phe Glu Lys Cys Cys Leu Ile Gly Cys Thr Lys Arg Ser Leu Ala Lys Tyr Cys.

Amino Acid Sequence of ProLXN: Lys Trp Lys Asp Asp Val Ile Lys Leu Cys Gly Arg Glu Leu Val Arg Ala Gln Ile Ala Ile Cys Gly Met Ser Thr Trp Ser Lys Arg Ser Leu Ser Gln Glu Asp Ala Pro Gln Thr Pro Arg Pro Val Ala Glu Ile Val Pro Ser Phe Ile Asn Lys Asp Thr Glu Thr Ile Ile Ile Met Leu Glu Phe Ile Ala Asn Leu Pro Pro Glu Leu Lys Ala Ala Leu Ser Glu Arg Gln Pro Ser Leu Pro Glu Leu Glu Gln Tyr Val Pro Ala Leu Lys Asp Ser Asn Leu Ser Phe Glu Glu Phe Lys Lys Leu Ile Arg Asn Arg Gln Ser Glu Ala Ala Asp Ser Asn Pro Ser Glu Leu Lys Tyr Leu Gly Leu Asp Thr His Ser Gln Lys Lys Arg Arg Pro Tyr Val Ala Leu Phe Glu Lys Cys Cys Leu Ile Gly Cys Thr Lys Arg Ser Leu Ala Lys Tyr Cys.

Amino Acid Sequence of Hb-α-(1-31): Val Leu Ser Pro Ala Asp Lys Thr Asn Val Lys Ala Ala Trp Gly Lys Val Gly Ala His Ala Gly Glu Tyr Gly Ala Glu Ala Leu Glu Arg.

Amino Acid Sequence of Hb-α-(32–141): Met Phe Leu Ser Phe Pro Thr Thr Lys Thr Tyr Phe Pro His Phe Asp Leu Ser His Gly Ser Ala Gln Val Lys Gly His Gly Lys Lys Val Ala Asp Ala Leu Thr Asn Ala Val Ala His Val Asp Asp Met Pro Asn Ala Leu Ser Ala Leu Ser Asp Leu His Ala His Lys Leu Arg Val Asp Pro Val Asn Phe Lys Leu Leu Ser His Cys Leu Leu Val Thr Leu Ala Ala His Leu Pro Ala Glu Phe Thr Pro Ala Val His Ala Ser Leu Asp Lys Phe Leu Ala Ser Val Ser Thr Val Leu Thr Ser Lys Tyr Arg.

Amino Acid Sequence of Hb-α: Val Leu Ser Pro Ala Asp Lys Thr Asn Val Lys Ala Ala Trp Gly Lys val Gly Ala His Ala Gly Glu Tyr Gly Ala Glu Ala Leu Glu Arg Met Phe Leu Ser Phe Pro Thr Thr Lys Thr Tyr Phe Pro His Phe Asp Leu Ser His Gly Ser Ala Gln Val Lys Gly His Gly Lys Lys Val Ala Asp Ala Leu Thr Asn Ala Val Ala His Val Asp Asp Met Pro Asn Ala Leu Ser Ala Leu Ser Asp Leu His Ala His Lys Leu Arg Val Asp Pro Val Asn Phe Lys Leu Leu Ser His Cys Leu Leu Val Thr Leu Ala Ala His Leu Pro Ala Glu Phe Thr Pro Ala Val His Ala Ser Leu Asp Lys Phe Leu Ala Ser Val Ser Thr Val Leu Thr Ser Lys Tyr Arg.

The present invention will be illustrated in more detail with reference to the following Examples, which should not be construed to be limiting the scope of the present invention.

EXAMPLE 1

10 mg of IFN-γ-(1–46) and 100 mg of IFN-γ-(47–146) (see Referential Example 1) are dissolved in 1 ml of DMF, followed by addition of 0.7 ml of 0.5M Tris buffer (pH 6.5) containing 4 mg of trypsin. The reaction was allowed to proceed at 35° C. for 25 hours. After completion of the reaction, the reaction liquid was applied to a column (2×40 cm) of Sephadex G-50 (manufactured and sold by Pharmacia Fine Chemicals, Inc., Sweden), and elution is performed with 0.4M acetic acid. Trypsin, IFN-γ, IFN-γ-(47–146), a dimer of IFN-γ-(1–46) and IFN-γ-(1–46) are eluted in this order. Fractions of IFN-γ are collected, and subjected to lyophilization. The resultant is applied to a column (2×40 cm) of DEAE-Sephadex A-25 (manufactured and sold by Pharmacia Fine Chemicals, Inc. Sweden), and elution is performed at 4° C. with a 7M urea-0.05M Tris buffer (pH 7.2) eluent with a salt gradient obtained by using 0 to 0.3M NaCl. IFN-γ fractions are collected, dialyzed against water, and subjected to lyophilization. As a result, 20 mg of IFN-γ is obtained.

The thus obtained IFN-γ has an antiviral activity of $10^8$ units/mg. The antiviral activity of the so-obtained INF-γ is measured in substantially the same manner as described in P. C. Merigan, A Plaque Inhibition Assay for Human Interferon Employing Human Neonate Skin Fibroblast Monolayers & Bovine Vesicular Stomatitis Virus, "In-vitro Method in Cell-Mediated Immunity," edited by E. D. B. R. Bloom & P. R. Grade, Academic Press, N.Y. 1971, pp. 489. Specifically, each peptide as obtained above is diluted and added to a growth medium containing 10% by volume of fetal calf serum. In the growth medium, a monolayer of FS-4 cell (human neonate skin fibroblast) is cultured. Eighteen hours later, infection with vesicular stomatitis virsus which are each capable of forming 20 plaques per cell is effected, and culturing is continued at 37° C. for one hour. Then, the cells are rinsed with two portions of the above-mentioned growth medium. Again, the cells are cultured in the growth medium at 37° C. for 24 hours. Generation of viruses is checked by microscopic observation of the cells. Any damage of the cells is ascribed to viruses.

The molecular weight, amino acid composition and amino acid sequence of the above-obtained IFN-γ are as follows:

Molecular weight: about 20,000 g/mol.

Amino Acid Composition (mole percent): histidine (1.4) tryptophan (0.6) lysine (13.6 ) arginine (5.5) aspartic acid/asparagine (13.6) serine (7.6) glutamic acid/-glutamine (11.3) threonine (3.4) glycine (3.4) proline (1.4) alanine (5.5) valine (5.5) ½ cystine (1.4) methionine (2.7) isoleucine (4.8) leucine (6.8) phenylalanine (6.8) tyrosine (3.4)

Amino Acid Sequence: Cys Tyr Cys Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln.

EXAMPLE 2

1 g of material N described below is dissolved in 100 ml of DMF. To the resultant, added, in sequence, are 20 ml of DMF containing 2N acetic acid and 3 ml of isoamyl nitrite, while cooling with ice and NaCl. After 10 minutes, the mixture is neutralized with 6 ml of triethylamine. The resultant is then added to 40 ml of DMF containing 6g of material C described below and 6 ml of triethylamine, followed by stirring at 4° C. for 48 hours, and then subjected to evaporation-removal of the solvent under reduced pressure. The residue left after the removal of the solvent is dissolved in a 3 w/v % aqueous ammonia, and the aqueous phase is washed with ethyl acetate, acidified with an aqueous 10% citric acid solution. The deposited substance is filterred out, washed with an aqueous 4 w/v % NaCl solution, followed by drying on sodium sulfate.

According to the method of Yajima et al [H. Yajima and N. Fujii: "Chemical Pharmaceutical Bulletin" vol. 29, p. 600 (1981)], the dried product is treated with methanesulfonic acid (hereinafter referred to as "MSA" for one hour to remove the protecting group. Thus, 1 g of TPA having the following amino acid sequence is obtained.

Material N (see Referential Example 2): Z(OMe)Ser Tyr Gln Val Ile Cys(MBzl) Arg(MBS) Asp(OBzl) Glu-(OBzl) Lys(Z) Thr $GlnNHNH_2$.

Material C (see Referential Example 2): Met Ile Tyr Gln Gln His Gln Ser Trp Leu Arg Pro Val Leu Arg Ser Asn Arg Val Glu Tyr Cys Trp Cys Asn Ser Gly Arg Ala Gln Cys His Ser Val Pro Val Lys* Ser Cys Ser Glu Pro Arg Cys Phe Asn Gly Gly Thr Cys Gln Gln Ala Leu Tyr Phe Ser Asp Phe Val Cys Gln Cys Pro Glu Gly Phe Ala Gly Lys* Cys Cys Glu Ile Asp Thr Arg Ala Thr Cys Tyr Glu Asp Gln Gly Ile Ser Tyr Arg Gly Thr Trp Ser Thr Ala Glu Ser Gly Ala Glu Cys Thr Asn Trp Asn Ser Ser Ala Leu Ala Gln Lys* Pro Tyr Ser Gly Arg Arg Pro Asp Ala Ile Arg Leu Gly Leu Gly Asn His Asn Tyr Cys Arg Asn Pro Asp Arg Asp Ser Lys* Pro Trp Cys Tyr Val Phe Lys* Ala Gly Lys* Tyr Ser Ser Glu Phe Cys Ser Thr Pro Ala Cys Ser Glu Gly Asn Ser Asp Cys Tyr Phe Gly Asn Gly Ser Ala Tyr Arg Gly Thr His Ser Leu Thr Glu Ser Gly Ala Ser Cys Leu Pro Trp Asn Ser Met Ile Leu Ile Gly Lys* Val Tyr Thr Ala Gln Asn Pro Ser Ala Gln Ala Leu Gly Leu Gly Lys* His Asn Tyr Cys Arg Asn Pro Asp Gly Asp Ala Lys* Pro Trp Cys His Val Leu Lys* Asn Arg Arg Leu Thr Trp Glu Tyr Cys Asp Val Pro Ser Cys Ser Thr Cys Gly Leu Arg Gln Tyr Ser Gln Pro Gln Phe Arg Ile Lys* Gly Gly Leu Phe Ala Asp Ile Ala Ser His Pro Trp Gln Ala Ala Ile Phe Ala Lys His Arg Arg Ser Pro Gly Glu Arg Phe Leu Cys Gly Gly Ile Leu Ile Ser Ser Cys Trp Ile Leu Ser Ala Ala His Cys Phe Gln Glu Arg Phe Pro Pro His His Leu Thr Val Ile Leu Gly Arg Thr Tyr Arg Val Val Pro Gly Glu Glu Glu Gln Lys* Phe Glu Val Glu Lys* Tyr Ile Val His Lys* Glu Phe Asp Asp Asp Thr Tyr Asp Asn Asp Ile Ala Leu Leu Gln Leu Lys* Ser Asp Ser Ser Arg Cys Ala Gln Glu Ser Ser Val Val Arg Thr Val Cys Leu Pro Pro Ala Asp Leu Gln Leu Pro Asp Trp Thr Glu Cys Glu Leu Ser Gly Tyr Gly Lys* His Glu Ala Leu Ser Pro Phe Tyr Ser Glu Arg Leu Lys* Glu Ala His Val Arg Leu Tyr Pro Ser Ser Arg Cys Thr Ser Gln His Leu Leu Asn Arg Thr Val Thr Asp Asn Met Leu Cys Ala Gly Asp Thr Arg Ser Gly Gly Pro Gln Ala Asn Leu His Asp Ala Cys Gln Gly Asp Ser Gly Gly Pro Leu Val Cys Leu Asn Asp Gly Arg Met Thr Leu Val Gly Ile Ile Ser Trp Gly Leu Gly Cys Gly Gln Lys* Asp Val Pro Gly Val Tyr Thr Lys* Val Thr Asn Tyr Leu Asp Trp Tle Arg Asp Asn Met Arg Pro (wherein "Lys*" represents ε-amidinate lysine).

Amino acid sequence of TPA: Ser Tyr Gln Val Ile Cys Arg Asp Glu Lys Thr Gln Met Ile Tyr Gln Gln His Gln Ser Trp Leu Arg Pro Val Leu Arg Ser Asn Arg Val Glu Tyr Cys Trp Cys Asn Ser Gly Arg Ala Gln Cys His Ser Val Pro Val Lys Ser Cys Ser Glu Pro Arg Cys Phe Asn Gly Gly Thr Cys Gln Gln Ala Leu Tyr Phe Ser Asp Phe Val Cys Cys Gln Cys Pro Glu Gly Phe Ala Gly Lys Cys Glu Ile Asp Thr Arg Ala Thr Cys Tyr Glu Asp Gln Gly Ile Ser Tyr Arg Gly Thr Trp Ser Thr Ala Glu Ser Gly Ala Glu Cys Thr Asn Trp Asn Ser Ser Ala Leu Ala Gln Lys Pro Tyr Ser Gly Arg Arg Pro Asp Ala Ile Arg Leu Gly Leu Gly Asn His Asn Tyr Cys Arg Asn Pro Asp Arg Asp Ser Lys Pro Trp Cys Tyr Val Phe Lys Ala Gly Lys Tyr Ser Ser Glu Phe Cys Ser Thr Pro Ala Cys Ser Glu Gly Asn Ser Asp Cys Tyr Phe Gly Asn Gly Ser Ala Tyr Arg Gly Thr His Ser Leu Thr Glu Ser Gly Ala Ser Cys Leu Pro Trp Asn Ser Met Ile Leu Ile Gly Lys Val Tyr Thr Ala Gln Asn Pro Ser Ala Gln Ala Leu Gly Leu Gly Lys His Asn Tyr Cys Arg Asn Pro Asp Gly Asp Ala Lys Pro Trp Cys His Val Leu Lys Asn Arg Arg Leu Thr Trp Glu Tyr Cys Asp Val Pro Ser Cys Ser Thr Cys Gly Leu Arg Gln Tyr Ser Gln Pro Gln Phe Arg Ile Lys Gly Gly Leu Phe Ala Asp Ile Ala Ser His Pro Trp Gln Ala Ala Ile Phe Ala Lys His Arg Arg Ser Pro Gly Glu Arg Phe Leu Cys Gly Gly Ile Leu Ile Ser Ser Cys Trp Ile Leu Ser Ala Ala His Cys Phe Gln Glu Arg Phe Pro Pro His His Leu Thr Val Ile Leu Gly Arg Thr Tyr Arg Val Val Pro Gly Glu Glu Glu Gln Lys Phe Glu Val Glu Lys Tyr Ile Val His Lys Glu Phe Asp Asp Asp Thr Tyr Asp Asn Asp Ile Ala Leu Leu Gln Leu Lys Ser Asp Ser Ser Arg Cys Ala Gln Glu Ser Ser Val Val Arg Thr Val Cys Leu Pro Pro Ala Asp Leu Gln Leu Pro Asp Trp Thr Glu Cys Glu Leu Ser Gly Tyr Gly Lys His Glu Ala Leu Ser Pro Phe Tyr Ser Glu Arg Leu Lys* Glu Ala His Val Arg Leu Tyr Pro Ser Ser Arg Cys Thr Ser Gln His Leu Leu Asn Arg Thr Val Thr Asp Asn Met Leu Cys Ala Gly Asp Thr Arg Ser Gly Gly Pro Gln Ala Asn Leu His Asp Ala Cys Gln Gly Asp Ser Gly Gly Pro Leu Val Cys Leu Asn Asp Gly Arg Met Thr Leu Val Gly Ile Ile Ser Trp Gly Leu Gly Cys Gly Gln Lys Asp Val Pro Gly Val Tyr Thr Lys Val Thr Asn Tyr Leu Asp Trp Ile Arg Asp Asn Met Arg Pro.

REFERENTIAL EXAMPLE 1

Step 1

(Benzoylation or Isobutylation)

A. Synthesis of N-benzoyl deoxyadenosine (hereinafter referred to as "dbzA")

50 mmol of deoxyadenosine (hereinafter referred to as "dA") is suspended in 150 ml of dry pyridine. 300 mmol of benzoylchloride is added dropwise while ice-cooling and then, the reaction mixture is warmed to room temperature, followed by stirring for about one hour. The completion of the reaction is confirmed by means of thin-layer chromatography (eluent: a 10:1 by volume mixture of chloroform and methanol). The reaction mixture is then poured into a mixture of 500 ml of chloroform, 350 g of ice and 28 g of sodium hydrogen-carbonate. The resulting mixture is shaken in a separatory funnel, allowed to stand, and then the chloroform phase is taken out. The aqueous phase is extracted with two portions of chloroform, and the chloroform phase is taken out. The chloroform phases obtained are mixed together and washed with two portions of water. Chloroform is distilled off, and 150 ml of ethanol and 100 ml of pyridine are added to the residue to obtain a homogeneous solution. The thus obtained homogeneous solution is chilled quickly to 0° C., and a mixture of 200 ml of 2N aqueous NaOH and 200 ml of ethanol is added while stirring to the solution, thereby to obtain a homogeneous solution. The resulting solution is stirred at room temperature for 5 minutes, cooled, and, after addition of 200 ml of 2N aqueous hydrochloric acid, concentrated to a half volume under reduced pressure. Thereafter, an equal amount of water is added to the thus concentrated solution, and benzoic acid is extracted out with diethyl ether. The aqueous phase is concentrated and subjected to azeotropic distillation with water. Thus, N-benzoyl deoxyadenosine (dbzA) is deposited. A small amount of pyridine is added to the thus obtained N-benzoyl deoxyadenosine, and the resulting mixture is, after allowed to stand overnight in a refrigerator, subjected to filtration. Thus, deposited crystals are filtered off. The crystals thus isolated are washed with a 5% by weight aqueous pyridine solution, and then with diethyl ether. As a result, 35 mmol of dbzA is obtained. The total yield of dbzA is 70%.

B. Synthesis of N-benzoyl deoxycytidine (hereinafter referred to as "dbzC")

100 mmol of deoxycytidine (hereinafter referred to as "dC") is suspended in 500 ml of pyridine. 1 equivalent of triethylamine is added to the resulting suspension, followed by stirring for 30 minutes. 6 equivalents of benzoyl chloride is then added with ice-cooling. Subsequently, the same procedures as employed in item A above are repeated, whereby benzoylation of dC is attained. After completion of the benzoylation reaction, chloroform is distilled off. The residue left after removal of chloroform is dissolved in a mixture of 1250 ml of tetrahydrofuran, 1 liter of methanol and 250 ml of water. 250 ml of 2N aqueous NaOH is added to the resulting solution with stirring while ice-cooling. After 10 minutes, the mixture is neutralized by addition of 250 ml of 2N aqueous HCl. The subsequent procedures are the same as in item A. As a result, N-benzoyl deoxycytidine (dbzC) is deposited.

C. Synthesis of isobutyl deoxyguanosine (hereinafter referred to as "dibG")

100 mmol of deoxyguanosine (hereinafter referred to as "dG") is suspended in 500 ml of pyridine. 6 equivalents of isobutyl chloride is added dropwise with ice-cooling. The so obtained reaction mixture is, after being stirred at 0° C. for 3 hours, subjected to the same treatment as employed in item B above, whereby isobutylation of dG is attained. After completion of the isobutylation reaction, chloroform is distilled off. The residue left after removal of chloroform is dissolved in 500 ml of ethanol, and then 500 ml of 2N aqueous NaOH is added at 0° C., followed by stirring for 15 minutes. The resulting mixture is then poured onto 1 liter of a ice-chilled, pyridinium type cation exchange resin (Dowex×50×2, manufactured and sold by Dow Chemical Co., U.S.A.), whereby neutralization is effected. The thus neutralized mixture is placed in a column packed with a small amount of the above-mentioned resin, and washed with a 10% (w/v) aqueous pyridine solution of which the volume is 3-fold the volume of the packed resin. The eluate and the washings are mixed and concentrated, and the residue is recrystallized from 500 ml of a 5% (w/v) aqueous pyridine solution, thereby to obtain dibG.

Step 2

(5'-dimethoxytritylation)

100 mmol of thymidine, 100 mmol of dbzA, 100 mmol of dbzC and 100 mmol of dibG are mixed with 200 ml, 400 ml, 400 ml and 750 ml of pyridine, respectively. Into each of the resulting mixtures, 1.1 equivalents of dimethoxy trityl chloride are added, and the reaction is allowed to proceed for 3 hours. The reaction is stopped by adding 50 ml of methanol. Each of the reaction mixtures is concentrated, dissolved in 50 ml of chloroform and washed with water. For isolation of 5'-dimethoxytritylthymidine [hereinafter referred to as "(DMTr)T"], the reaction mixture is subjected to evaporation to remove the solvent, and then subjected to azeotropic distillation with toluene, dissolved in 1500 ml of benzene, heated, charged with n-hexane until the mixture becomes opaque, and allowed to stand at 4° C. to recrystallize (DMTr)T therefrom. For isolation of (DMTr)dbzA, (DMTr)dbzC and (DMTr)dibG, each reaction mixture is subjected to evaporation to remove the solvent, dissolved in chloroform, and subjected to chromatography employing 1.5 kg of silica gel, in which elution is performed with a 3% by weight aqueous methanol.

Step 3

(Synthesis of a dimer and a trimer)

6 mmol of (DMTr)dibG is subjected to azeotropic distillation with pyridine and then dissolved in 10 ml of pyridine, p-chlorophenyl phosphorodichloride is added dropwise, with stirring on ice, to a mixture of 1.5×2.2 equivalents of triazole, 1.5×2.2 equivalents of triethylamine and 20 ml of dioxane, while insulating from moisture. After stirring for one hour at room temperature, triethylamine hydrochloric acid is filtered out. The filtrate is added to the above-obtained pyridine solution of (DMTr)dibG, while insulating from moisture. After evaporation-removal of approximately $\frac{1}{4}$ the volume of the solvent, the solution is allowed to stand for one hour at room temperature. Then, 4 equivalents of 1-methylimidazol and 8 mmol of dibG are added, and the resulting mixture is subjected to azeotropic distillation with pyridine. The residue is dissolved in 60 ml of pyridine. 9 mmol of triisopropylbenzenesulfonylnitroimidazolide (hereinafter referred to as "TPSNI") is charged in the thus obtained pyridine solution. The resulting mixture is concentrated to a $\frac{1}{4}$ volume, and then allowed to stand overnight at 30° C.

The reaction is stopped by addition of 6 ml of a 50 wt % aqueous pyridine solution. After evaporation-removal of the solvent, the mixture is passed through a column packed with 150 g of Type 60 silica gel (manufactured and sold by Wako Junyaku Kogyo, K.K., Japan). The developed product is eluted with a 30:1 by volume mixture of methylene chloride and methanol (pyridine content: 1%). The eluate is concentrated, and then charged with n-hexane, to deposit the desired dimer in the form of a powder.

2 mmol of the thus obtained dimer is phosphated in substantially the same manner as mentioned above.

The thus phosphated dimer is subjected to azeotropic distillation with pyridine. The residue is dissolved in 20 ml of pyridine. 3 ml of TPSNI is charged in the resulting pyridine solution, and condensation is effected in the same manner as mentioned above. 21 hours later, the reaction is stopped by addition of 2 ml of a 50% by weight aqueous pyridine solution. 20 ml of chloroform is added, and the reaction mixture is washed twice with 15 ml of 0.1M aqueous tetraethylammonium bromide (hereinafter referred to as "TEAB"). After evaporation-removal of the solvent, the desired trimer is isolated by the use of 60 g of silica gel. The total yield of the trimer is 60%.

Step 4

(Removal of protecting group from the trimer 20 mg of the trimer obtained in Step 3 above is dissolved in 3 ml of pyridine. 15 ml of a concentrated aqueous ammonia is added to the above-obtained pyridine solution, the reaction vessel is sealed, and the mixture is then allowed to stand for 19 hours at room temperature. Thereafter, the reaction mixture is heated to 55° C. for 5 hours, thereby to distill ammonia off. Further, 20 ml of 80% by volume aqueous acetic acid is added to the reaction mixture, and then acetic acid is distilled off. The reaction mixture is then subjected to azeotropic distillation with toluene and the residue is dissolved in 25 ml of 0.1M aqueous TEAB, and washed with 25 ml of chloroform three times and then with 25 ml of diethyl ether. The resulting solution is subjected to evaporation to remove the solvent, and the residue is dissolved in 16 ml of 7M urea containing 20 mM Tris-$CH_3COOH$ (pH 8.0). The thus obtained mixture is passed through a column packed with DEAE cellulose, and eluted with a 7M urea-0.02M Tris-$CH_3COOH$ (pH 8) eluent with a salt gradient (using 500 ml of 0.05M NaCl and 500 ml of 0.40M NaCl). Fractions each exhibiting peak absorbance are collected, whereby the trimer is obtained.

Step 5

(Synthesis of oligodeoxyribonucelotide)

Oligodeoxyribonucleotides are prepared in the same manner as mentioned in Step 3. The protecting groups are removed from the obtained oligodeoxyribonucleotides in the same manner as mentioned in Step 4, thereby to obtain the following oligodeoxyribonucleotides. In the following oligodeoxyribonucleotides, A stands for a 2'-deoxyadenylic acid residue, G a 2'-deoxyguanylic acid residue, C a 2'-deoxycytidylic acid residue and T a thymidylic acid residue and the left end of the genetic code and the right end of the genetic code represent 5'-hydroxyl group side and 3'-hydroxyl group side, respectively.

(1) G A T C C A T G T G T T A C T G T
(2) C A A G A C C C A T A C
(3) G T T A A G G A A G C T
(4) G A A A A C T T G A A G
(5) A A G T A C T T T A A C
(6) G C T G G T C A C T C T
(7) G A C G T T G C T G A C
(8) A A C G G T A C T T T G
(9) T T T T T G G G T A T C
(10) T T G A A G A A C T G G
(11) A A G G A A G A A T C T
(12) G A C A G A A A G T A A G
(13) T C G A C T T A C T T
(14) T C T G T C A G A T T C
(15) T T C C T T C C A G T T
(16) C T T C A A G A T A C C
(17) C A A A A A C A A A G T
(18) A C C G T T G T C A G C
(19) A A C G T C A G A G T G
(20) A C C A G C G T T A A A
(21) G T A C T T C T T C A A
(22) G T T T T C A G C T T C
(23) C T T A A C G T A T G G
(24) G T C T T G A C A G T A A C A C A T G

Step 6

(Synthesis of polydeoxyribonucleotide)

40 pico mol each of the oligodeoxyribonucleotides (1) and (2) obtained in Step 5 above and 6.5 units of T4 DNA kinase are put in 25 μl of a mixture of 80 pico mol of [$\gamma$-$^{32}$P]ATP(8 Ci/mmol), 100 μM spermidine, 20 mM DDT, 10 mM $MgCl_2$, 50 mM Tris-HCl (pH 9) and 0.1 mM EDTA. The reaction is allowed to proceed for 30 minutes at 37° C., whereby (1) and (2) are bonded to obtain (1)-(2). Ethanol is added to the reaction mixture in a volume 2.5 times that of the reaction mixture, causing the oligomer to precipitate. Electrophoresis is effected on a 20% polyacrylamide gel in 7M urea, thereby to attain separation of (1)-(2).

(1)-(2) G A T C C A T G T G T T A C T G T C A A G A C C C A T A C (3) and (4) are bonded in the same manner as mentioned above, thereby to obtain (3)-(4). Separation of (3)-(4) is effected in the same manner as mentioned above. Further, the above-obtained (1)-(2) and (3)-(4) are bonded, thereby to obtain (1)-(2)-(3)-(4). The above operation is repeated. Thus, the following DNAs are obtained.

(1)-(2)-(3)-(4)-(5)-(6)-(7)-(8)-(9)-(10)-(11)-(12), and
(13)-(14)-(15)-(16)-(17)-(18)-(19)-(20)-(21)-(22)-(23)-(24)

(1)-(12) and (13)-(24) are mixed in a 50 μl TNE buffer solution (an aqueous solution containing 50 mM of Tris-HCl (pH 7.5), 100 mM of NaCl and 5 mM of ethylenediaminetetraacetic acid). The mixture is incubated for one hour at a temperature of each of 65° C., 45° C., 37° C. and 20° C. Then, the mixture is added to a 20 μl mixture containing 100 mM Tris-HCl (pH 7.5), 100 mM $CaCl_2$ and 100 mM $MgCl_2$, followed by cooling on ice for 20 minutes.

Step 7

(Cloning)

In accordance with the procedure described in A. J. Twigg et al., Nature, 283, 216 (1980), pAT 153 plasmid is prepared. From the thus obtained pAT 153 plasmid, pPM 50 plasmid having a lac promotor and a lac operator is produced in accordance with the procedure described in Michael D. Edge et al., Nature, 292, 756–762 (1981). 4 μg of pPM 50 plasmid DNA is cleaved in a mixture of 10 mM Tris-HCl (pH 7.6), 6 mM $MgCl_2$, 150 mM NaCl and 1 mM dithiothreitol (Cleland's reagent) (hereinafter referred to as "DTT") for 60 minutes at 37° C. with restriction enzymes, BamHI and Sal I. After termination of the reaction, DNA is extracted with a 3:1 by volume mixture of phenol and chloroform, and fragments are separated by electrophoresis effected on a 1% agarose gel in a mixture of 40 mM Tris-HCl (pH 7.8), 6 mM sodium acetate and 1 mM ethylenediaminetetraacetic acid (hereinafter referred to as "EDTA"). Fragments which are larger in size are recovered. 1 μg of the so obtained BamHI-Sal I 3.2 kb vector fragment and the chemically synthesized gene obtained in Step 6 above are ligated in 30 μl of a mixture of 20 mM Tris-HCl (pH 7.6), 10 mM $MgCl_2$ and 10 mM DTT, containing 0.4 unit of T4 DNA ligase. The reaction is allowed to proceed for 16 hours at 12° C. As a result, there is obtained a plasmid containing DNA in which the chemically synthesized gene obtained in Step 6 above is bonded to the end of the lactose operon.

The thus obtained plasmid is contacted with *E. coli* $\chi$1776 (ATCC accession number 31244), thereby to transform the *E. coli* $\chi$1776. The resulting transformants are cultured in nutrient broth for 16 hours at 37° C. to prepare DNA. The thus prepared DNA is analyzed with respect to the DNA deoxyribonucleotide sequence in accordance with the procedure described in A. M. Maxam et al., Proc. Natl. Acad. Sci. USA, 74, 560–564 (1978). The result shows that the analyzed sequence is in agreement with the theoretical sequence.

Step 8

(Production of peptide)

*E. coli* cells producing the intended peptide is cultured and subjected to bacteriolysis. After the nucleic acid in the solution containing *E. coli* cells subjected to bacteriolysis is decomposed by ribonuclease and deoxyribonuclease, the solution is subjected to salting out using a 65% saturation aqueous solution of ammonium sulfate to precipitate the intended peptide. The fraction containing the precipitate is subjected to purification procedure using controlled pore glass beads, thereby to obtain the intended peptide.

The amino acid sequence of the peptide is determined in the following way. First, the methionyl linkage of the peptide is severed with cyanogen bromide. Second, the obtained peptide fragments are separated using a column in which Sephadex G-100 (manufactured and sold by Pharmacia Fine Chemicals, Inc., Sweden) (hereinafter referred to as "Sephadex G-100 column") and the amino acid sequence of each of the fragments is determined successively from the N-terminus thereof by known high precision amino acid sequence analysis. On the other hand, the above-obtained peptide is partially cleaved with trypsin and the resulting peptide fragments are separated using a Sephadex G-100 column. The amino acid sequence of each of the separated fragments is determined successively from the N-terminus thereof in the same manner as mentioned above. By comparing the amino acid sequences of the peptide fragments obtained by the cleavage with cyanogen bromide with those obtained by the cleavage with trypsin, the arrangement of the fragments of the above peptide is determined. Thus, the amino acid sequence of the above peptide is obtained as follows.

IFN-γ-(1-46) to which methionine is bonded at its N-terminus [hereinafter referred to as "Met-IFN-γ-(1-46)"]: Met Cys Tyr Cys Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile leu Lys Asn Trp Lys Glu Glu Ser Asp Arg Lys.

Step 9

(Cleavage by cyanogen bromide)

10 μmol of the peptide obtained in Step 8 above is dissolved in 13.7 ml of 0.1N HCl. To the solution is added 127 mg of crystalline cyanogen bromide and the reaction is allowed to proceed at room temperature for 24 hours while stirring. After the reaction product is lyophilized, the product is dissolved in 0.2N acetic acid and subjected to gel chromatography using a column (6×120 cm) in which Sephadex G-25 (manufactured and sold by Pharmacia Fine Chemicals, Inc., Sweden) is packed. The peptide fractions are collected, dialyzed against distilled water and lyophilized. The yield is 80%. The amino acid sequence of the lyophilized peptide is determined in accordance with the procedure described in Step 8 above. The amino acid sequence of the peptide is as follows.

IFN-γ-(1-46): Cys Tyr Cys Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys.

Step 10

(Synthesis of oligodeoxyribonucleotide)

The following oligodeoxyribonucleotides are prepared in the same manner as mentioned in Step 5 above.

(1) G A T C C A T G C A A T C T C A A
(2) A T C G T T T C T T T T
(3) T A C T T T A A G T T G
(4) T T T A A G A A C T T T
(5) A A G G A C G A C C A A
(6) T C T A T C C A A A A G
(7) T C T G T T G A A A C T
(8) A T C A A G G A A G A C
(9) A T G A A C G T T A A G
(10) T T T T T T A A C T C T
(11) A A C A A G A A G A A G
(12) A G A G A C G A C T T T
(13) G A A A A G T T G A C T
(14) A A C T A C T C T G T T
(15) A C T G A C T T G A A C
(16) G T T C A A A G A A A G
(17) G C T A T C C A C G A A
(18) T T G A T C C A A G T T
(19) A T G G C T G A A T T G
(20) T C T C C A G C T G C T
(21) A A G A C T G G T A A G
(22) A G A A A G A G A T C T
(23) C A A A T G T T G T T T
(24) A G A G G T A G A A G A
(25) G C T T C T C A A T A A G
(26) T C G A C T T A T T G A G A A G C T C T T C T
(27) A C C T C T A A A C A A
(28) C A T T T G A G A T C T
(29) C T T T C T C T T A C C
(30) A G T C T T A G C A G C
(31) T G G A G A C A A T T C
(32) A G C C A T A A C T T G
(33) G A T C A A T T C G T G
(34) G A T A G C C T T T C T
(35) T T G A A C G T T C A A
(36) G T C A G T A A C A G A
(37) G T A G T T A G T C A A
(38) C T T T T C A A A G T C
(39) G T C T C T C T T C T T
(40) C T T G T T A G A G T T
(41) A A A A A A C T T A A C
(42) G T T C A T G T C T T C
(43) C T T G A T A G T T T C
(44) A A C A G A C T T T T G
(45) G A T A G A T T G G T C
(46) G T C C T T A A A G T T
(47) C T T A A A C A A C T T
(48) A A A G T A A A A A G A
(49) A A C G A T T T G A G A
(50) T T G C A T C A T G

Step 11

(Synthesis of polydeoxyribonucleotide)

Substantially the same procedures as described in Step 6 are repeated except that the oligodeoxyribonucleotides obtained in Step 10 are used instead of the oligodeoxyribonucleotides used in Step 6 above. Thus, there is obtained a double stranded DNA consisting of the following deoxyribonucleotides (1)-(2)-(3)-(4)-(5)-(6)-(7)-(8)-(9)-(10)-(11)-(12)-(13)-(14)-(15)-(16)-(17)-(18)-(19)-(20)-(21)-(22)-(23)-(24)-(25), stranded with
(26)-(27)-(28)-(29)-(30)-(31)-(32)-(33)-(34)-(35)-(36)-(37)-(38)-(39)-(40)-(41)-(42)-(43)-(44)-(45)-(46)-(47)--(48)-(49)-(50)

Step 12

(Cloning)

Substantially the same procedures as described in Step 7 above are repeated except that the double stranded DNA obtained in Step 11 above is used. There are obtained transformants containing the DNA having the deoxyribonucleotide sequences as described in Step 11 above.

Step 13

(Production of peptide)

A peptide is produced in the same manner as described in Step 8 except that the transformant obtained in Step 12 above is used instead of the transformant used in Step 8 above. The amino acid sequence of the peptide is determined in the same manner as described in Step 8 above. The amino acid sequence of the peptide is shown below.

IFN-γ-(48∼146): Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg

Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln.

Step 14

[Conversion of ε-amino groups of IFN-γ-(48–146) to amidino groups]

1 g of IFN-γ-(48–146) is dissolved in 200 ml of water at 40° C. To the obtained solution is gradually added 0.2 g of basic copper carbonate [$CuCO_3.Cu(OH)_2$]. After 24 hours, the reaction mixture is filtered at 40° C. The filtrate is concentrated to obtain a copper salt of IFN-γ-(48–146).

75 mg of the obtained copper salt of IFN-γ-(48–146) is dissolved in 2 ml of water and adjusted to have a pH value of 10.3 using 1M HCl. 82.5 mg of acetimidic acid methyl ester hydrochloride is dissolved in an equimolar amount of 2M NaOH to attain neutralization. Immediately thereafter, IFN-γ-(48–146) solution is added. The reaction liquid is readjusted to pH 10.3 and reaction is allowed to proceed at room temperature for 40 minutes. During the reaction, the pH of the reaction liquid is kept at 10.3 by adding 1M HCl. The reaction is stopped by neutralizing the reaction liquid with 1M HCl. After dialyzed against water, the reaction liquid is lyophilized to obtain 70 mg of IFN-γ-(48–146) in which the ε-amino groups of lysines are converted to amidino groups [ε-amidino-lysine IFN-γ-(48–146)].

Step 15

50 mg of Boc-Ile-$NHNH_2$ is dissolved in 10 ml of DMF. Under cooling on a mixture of ice and sodium chloride, 2.2 ml of 1.8N hydrogen chloride dissolved in DMF and 0.3 ml of isoamyl nitrite are successively added to the obtained solution. After 10 minutes, the solution is neutralized with 0.5 ml of triethylamine. The resulting solution is is added to 4 ml of an aqueous solution containing 50 mg of ε-amidino-lysine IFN-γ-(48–146) obtained in Step 14 and 0.6 ml of triethylamine and the reaction is allowed to proceed at 4° C. for 48 hours while stirring. Then, the solvent is distilled off under reduced pressure. The remainder is dissolved in 6 ml of trifluoroacetic acid and allowed to stand at room temperature for 20 minutes, followed by concentration at 40° C. or below. Diethyl ether is added to the obtained oily residue to obtain a precipitate. The precipitate is filtered off and washed with diethyl ether to obtain 40 mg of Ile-IFN-γ-(48–146), namely IFN-γ-(47–148).

The amino acid sequence analysis of IFN-γ-(47–148) shows that IFN-γ-(47–148) has the following amino acid sequence.

IFN-γ-(47–148): Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp Leu Asn Val Gln Arg Lys Ala Ile His Glu Leu Ile Gln Val Met Ala Glu Leu Ser Pro Ala Ala Lys Thr Gly Lys Arg Lys Arg Ser Gln Met Leu Phe Arg Gly Arg Arg Ala Ser Gln.

REFERENTIAL EXAMPLE 2

Step 1

(Amino acid azide to which protecting group is bonded)

According to the method described in A. Neuberger and F. Sanger, Biochemical Journal, Vol. 37, p. 515 (1943), 6 g of N-ε-benzyloxycarbonyllysine (hereinafter referred to as "Lys(Z)") is prepared from 10 g of lysine hydrochloride.

8 g of γ-benzyl glutamate (hereinafter referred to as "Glu(OBzl)") is prepared from 10 g of glutamine in accordance with the method described in Tadao Hayakawa et al, Journal of Chemical Society of Japan, Vol. 82, p. 601 (1961), and 5 g of γ-benzyl asparaginate (hereinafter referred to as "Asp(OBzl)") is prepared from 10 g of asparatic acid.

In accordance with the method described in O. Nishimura and M. Fujino, Chemical Pharmaceutical Bulletin, vol. 24, p. 1568 (1976), 5 g of NG-(p-methoxybenzenesulfonyl)arginine (hereinafter referred to as "Arg(MBS)") is prepared from 10 g of arginine hydrochloride.

8 g of S-(p-methoxybenzyl)cystine (hereinafter referred to as "Cys(MBzl)") is prepared from 10 g of cystine in accordance with the method described in S. Akabori et al, Journal of Chemical Society of Japan, Vol. 37, p. 433 (1964).

In accordance with the method described in F. Waygand and H. Hunger, Chem. Ber., Vol. 95, p. 1 (1962), predetermined kinds of p-methoxybenzyloxycarbonyl amino acids, namely, 4 g of each of Z(OMe(Gln, Z(OMe)Thr, Z(OMe)Lys(Z), Z(OMe)Glu(OBzl), Z(OMe)Asp(OBzl), Z(OMe)Arg(MBS), Z(OMe)Cys(MBzl), Z(OMe)Ile, Z(OMe)Val, Z(OMe)Tyr and Z(OMe)Ser are prepared respectively from 5 g of each of Gln, Thr, Lys(Z), Glu(OBzl), Asp(OBzl), Arg(MBS), Cys(MBzl), ILe, Val, Tyr, and Ser.

The Z(OMe) amino acid esters, namely, Z(OMe)Gln(OMe), Z(OMe)Thr(OMe), Z(OMe)Lys(Z)(OMe), Z(OMe)Glu(OBzl)(OMe), Z(OMe)Asp(OBzl)(OMe), Z(OMe)Arg(MBS)(OMe), Z(OMe)Cys(MBzl)(OMe), Z(OMe)Ile(OMe), Z(OMe)Val(OMe), Z(OMe)Tyr(OMe) and Z(OMe)Ser(OMe), are prepared, in a respective amount of 4 g, respectively from 4 g of the corresponding Z(OMe) amino acids mentioned above according to the process of H. Yajima et al, Chemical Pharmaceutical Bulletin, vol. 22, p. 1079 (1974).

Then, the Z(OMe) amino acid azides, namely, Z(OMe)Gln$N_3$, Z(OMe)Thr$N_3$, Z(OMe)Lys(Z)$N_3$, Z(OMe)Glu(OBzl)$N_3$, Z(OMe)Asp(OBzl)$N_3$, Z(OMe)Arg(MBS)$N_3$, Z(OMe)Cys(MBzl)$N_3$, Z(OMe)Ile$N_3$, Z(OMe)Val$N_3$, Z(OMe)Tyr(OMe)$N_3$ and Z(OMe)Ser$N_3$, are prepared, in a respective amount of 3 g, respectively from 4 g of the corresponding Z(OMe) amino acid esters mentioned above according to the process of J. Honzl and J. Rudinger, Collect. Czech. Chem. Commun., vol. 26, p. 2333 (1961).

According to the process of H. Watanabe et al, Chemical Pharmaceutical Bulletin, vol. 22, p. 1889 (1974), 4 g of Gln(OMe) is reacted with 4 g of β,β,β-trichloroethyloxycarbonylhydrazine (hereinafter referred to as "Troc$NHNH_2$") to obtain 3 g of GlnNHNH-Troc.

Step 2

(Synthesis of material N)

According to the process of H. Yajima et al, Chemical Pharmaceutical Bulletin, vol. 22, p. 1079 (1974), 3 g of Z(OMe)ThrNHNH$_2$ is reacted with 3 g of GlnNHNH-Troc to obtain 6 g of Z(OMe)Thr-GlnNHNH-Troc, which is subjected to trifluoroacetic acid treatment to obtain 5 g of Thr-Gln-NHNH-Troc. In substantially the same manner as described above, 3 g of Z(OMe)Lys(Z)NHNH$_2$ is reacted with 5 g of Thr-GlnNHNH-Troc to obtain Z(OMe)Lys(Z)-Thr-GlnNHNH-Troc, which is subjected to TFA treatment to obtain Lys(Z)-Thr-GlnNHNH-Troc. Further, in substantially the same manner as described above, 12 g of Z(OMe)Ser-Tyr-Gln-Val-Ile-Cys(MBzl)-Arg(MBS)-Asp(OBzl)-Glu(OBzl)-Lys(Z)-Thr-GlnNHNH-Troc is obtained. Then, 11 g of Z(OMe)Ser-Tyr-Gln-Val-Ile-Cys(MBzl)-Arg(MBS)-Asp(OBzl)-Glu(OBzl)-Lys(Z)-Thr-GlnNHNH$_2$ is obtained according to the process of H. Watanabe et al, Chemical Pharmaceutical Bulletin, vol. 22, p. 1889 (1974).

Step 3

(Transformation of *E. coli* χ1776)

Substantially the same procedures as described in Steps 1 to 6 of Referential Example 1 are repeated except that the below-mentioned oligodeoxyribonucleotides are used instead of the oligodeoxyribonucleotides in Step 5 of Referential Example 1. Thus, there is obtained a transformant of *E. coli* χ1776 containing plasmids having a double stranded DNA consisting of (1)-(2)-(3)-(4)-(5)-(6)-(7)-(8)-(9)-(10)-(11)-(12)-(13)-(14)-(15)-(16)-(17)-(18)-(19)-(20)-(21) (22)-(23)-(24)-(25)-(26)-(27)-(28)-(29)-(30)-(31)-(32)-(33)--(34)-(35)-(36)-(37)-(38)-(39)-(40)-(41)-(42)-(43)-(44)-(45-)-(46)-(47)-(48)-(49)-(50)-(51)-(52)-(53)-(54)-(55)-(56)-(57)-(58)-(59)-(60)-(61)-(62)-(63)-(64)-(65)-(66)-(67)-(68)-(69)-(70)-(71)-(72)-(73)-(74)-(75)-(76)-(77)-(78)-(79)-(80)--(81)-(82)-(83)-(84)-(85)-(86); stranded with (87)-(88)-(89)-(90)-(91)-(92)-(93)-(94)-(95)-(96)-(97)-(98)--(99)-(100)-(101)-(102)-(103)-(104)-(105)-(106)-(107)-(108)-(109)-(110)-(111)-(112)-(113)-(114)-(115)-(116)-(117)-(118)-(119)-(120)-(121)-(122)-(123)-(124)-(125)-(126)-(127)-(128)-(129)-(130)-(131)-(132)-(133)-(134)-(135)-(136-)-(137)-(138)-(139)-(140)-(141)-(142)-(143)-(144)-(145)-(146)-(147)-(148)-(149)-(150)-(151)-(152)-(153)-(154)-(155)-(156)-(157)-(158)-(159)-(160)-(161)-(162)-(163)-(164)-(165)-(166)-(167)-(168)-(169)-(170)-(171)-(172).

Olygodeoxyribonucleotides:

(1) G A T C C A T G A T A T A C C A G C A A
(2) C A T C A G T C A T G G C T G C G C
(3) C C T G T G C T C A G A A G C A A C
(4) C G G G T G G A A T A T T G C T G G
(5) T G C A A G A G T G G C A G G G C A
(6) C A G T G C C A C T C A G T G C C T
(7) G T C A A A A G T T G C A G C G A G
(8) C C A A G G T G T T T C A A C G G G
(9) G G C A C C T G C C A G C A G G C C
(10) C T G T A C T T C T C A G A T T T C
(11) G T G T G C C A G T G C C C C G A A
(12) G G A T T T G C T G G G A A G T G C
(13) T G T G A A A T A G A T A C C A G G
(14) G C C A C G T G C T A C G A G G A C
(15) C A G G G C A T C A G C T A C A G G
(16) G G C A C G T G G A G C A C A G C G
(17) G A G A G T G G T G C C G A G T G C
(18) A C C A A C T G G A A C A G C A G C
(19) G C G T T G G C C C A G A A G C C C
(20) T A C A G C G G G C G G A G G C C A
(21) G A C G C C A T C A G G C T G G G C
(22) C T G G G G A A C C A C A A C T A C
(23) T G C A G A A A C C C A G A T C G A
(24) G A C T C A A A G C C C T G G T G C
(25) T A C G T C T T T A A G G C G G G G
(26) A A G T A C A G C T C A G A C T T C
(27) T G C A G C A C C C C T G C C T G C
(28) T C T G A G G A A A C A G T G A C
(29) T G C T A C T T T G G G A A T G G G
(30) T C A G C C T A C C G T G G C A C G
(31) C A C A G C C T C A C C G A G T C G
(32) G G T G C C T C C T G C C T C C C G
(33) T G G A A T T C C A T G A T C C T G
(34) A T A G G C A A G G T T T A C A C A
(35) G C A C A G A A C C C C A G T G C C
(36) C A G G C A C T G G G C C T G G G C
(37) A A A C A T A A T T A C T G C C G G
(38) A A T C C T G A T G G G G A T G C C
(39) A A G C C C T G G T G C C A C G T G
(40) C T G A A G A A C C G C A G G C T G
(41) A C G T G G G A G T A C T G T G A T
(42) G T G C C C T C C T G C T C C A C C
(43) T G C G G C C T G A G A C A G T A C
(44) A G C C A G C C T C A G T T T C G C
(45) A T C A A A G G A G G G C T C T T C
(46) G C C G A C A T C G C C T C C C A C
(47) C C C T G G C A G G C T G C C A T C
(48) T T T G C C A A G C A C A G G A G G
(49) T C G C C C G G A G A G C G G T T C
(50) C T G T G C G G G G G C A T A C T C
(51) A T C A G C T C C T G C T G G A T T
(52) C T C T C T G C C G C C C A C T A C
(53) T T C C A G G A G A G G T T T C C G
(54) C C C C A C C A C C T G A C G G T G
(55) A T C T T G G G C A G A A C A T A C
(56) C G G G T G G T C C C T G G C G A G
(57) G A G G A G C A G A A A T T T G A A
(58) G T C G A A A A A T A C A T T G T C
(59) C A T A A G G A A T T C G A T G A T
(60) G A C A C T T A C G A C A A T G A C
(61) A T T G C G C T G C T G C A G C T G
(62) A A A T C G G A T T C G T C C C G C
(63) T G T G C C C A G G A G A G C A G C
(64) G T G G T C C G C A C T G T G T G C
(65) C T T C C C C C G G C G G A C C T G
(66) C A G C T G C C G G A C T G G A C G
(67) G A G T G T G A G C T C T C C G G C
(68) T A C G G C A A G C A T G A G G C C
(69) T T G T C T C C T T T C T A T T C G
(70) G A G C G G C T G A A G G A G G C T
(71) C A T G T C A G A C T G T A C C C A
(72) T C C A G C C G C T G C A C A T C A
(73) C A A C A T T T A C T T A A C A G A
(74) A C A G T C A C C G A C A A C A T G
(75) C T G T G T G C T G G A G A C A C T
(76) C G G A G C G G C G G G C C C C A G
(77) G C A A A C T T G C A C G A C G C C
(78) T G C C A G G G C G A T T C G G G A
(79) G G C C C C C T G G T G T G T C T G
(80) A A C G A T G G C C G C A T G A C T
(81) T T G G T G G G C A T C A T C A G C
(82) T G G G G C C T G G G C T G T G G A
(83) C A G A A G G A T G T C C C G G G T
(84) G T G T A C A C A A A G G T T A C C
(85) A A C T A C C T A G A C T G G A T T

(86) C G T G A C A A C A T G C G A C C G T G A G
(87) T C G A C T C A C G G T C G C A T G T T G T C A C G
(88) A A T C C A G T C T A G G T A G T T
(89) G G T A A C C T T T G T G T A C A C
(90) A C C C G G G A C A T C C T T C T G
(91) T C C A C A G C C C A G G C C C C A
(92) G C T G A T G A T G C C C A C C A A
(93) A G T C A T G C G G C C A T C G T T
(94) C A G A C A C A C C A G G G G G C C
(95) T C C C G A A T C G C C C T G G C A
(96) G G C G T C G T G C A A G T T T G G
(97) C T G G G G C C C G C C G C T C C G
(98) A G T G T C T C C A G C A C A C A G
(99) C A T G T T G T C G G T G A C T G T
(100) T C T G T T A A G T A A A T G T T G
(101) T G A T A T G C A G C G G C T G G A
(102) T G G G T A C A G T C T G A C A T G
(103) A G C C T C C T T C A G C C G C T C
(104) C G A A T A G A A A G G A G A C A A
(105) G G C C T C A T G C T T G C C G T A
(106) G C C G G A G A G C T C A C A C T C
(107) C G T C C A G T C C G G C A G C T G
(108) C A G G T C C G C C G G G G G A A G
(109) G C A C A C A G T G C G G A C C A C
(110) G C T G C T C T C C T G G G C A C A
(111) G C G G G A C G A A T C C G A T T T
(112) C A G C T G C A G C A G C G C A A T
(113) G T C A T T G T C G T A A G T G T C
(114) A T C A T C G A A T T C C T T A T G
(115) G A C A A T G T A T T T T T C G A C
(116) T T C A A A T T T C T G C T C C T T C
(117) C T C G C C A G G G A C C A C C C G
(118) G T A T G T T C T G C C C A A G A T
(119) C A C C G T C A G G T G G T G G G G
(120) C G G A A A C C T C T C C T G G A A
(121) G C A G T G G G C G G C A G A G A G
(122) A A T C C A G C A G G A G C T G A T
(123) G A G T A T G C C C C C G C A C A G
(124) G A A C C G C T C T C C G G G C G A
(125) C C T C C T G T G C T T G G C A A A
(126) G A T G G C A G C C T G C C A G G G
(127) G T G G G A G G C G A T G T C G G C
(128) G A A G A G C C C T C C T T T G A T
(129) G C G A A A C T G A G G C T G G C T
(130) G T A C T G T C T C A G G C C G C A
(131) G G T G G A G C A G G A G G G C A C
(132) A T C A C A G T A C T C C C A C G T
(133) C A G C C T G C G G T T C T T C A G
(134) C A C G T G G C A C C A G G G C T T
(135) G G C A T C C C C A T C A G G A T T
(136) C C G G C A G T A A T T A T G T T T
(137) G C C C A G G C C C A G T G C C T G
(138) G G C A C T G G G G T T C T G T G C
(139) T G T G T A A A C C T T G C C T A T
(140) C A G G A T C A T G G A A T T C C A
(141) C G G G A G G C A G G A G G C A C C
(142) C G A C T C G G T G A G G C T G T G
(143) C G T G C C A C G G T A G G C T G A
(144) C C C A T T C C C A A A G T A G C A
(145) G T C A C T G T T T C C C T C A G A
(146) G C A G G C A G G G G T C C T G C A
(147) G A A G T C T G A G C T G T A C T T
(148) C C C C G C C T T A A A G A C G T A
(149) G C A C C A G G G C T T T G A G T C
(150) T C G A T C T G G G T T T C T G C A
(151) G T A G T T G T G G T T C C C C A G
(152) G C C C A G C C T G A T G G C G T C
(153) T G G C C T C C G C C C G C T G A T
(154) G G G C T T C T G G G C C A A C G C
(155) G C T G C T G T T C C A G T T G G T
(156) G C A C T C G G C A C C A C T C T C
(157) C G C T G T G C T C C A C G T G C C
(158) C C T G T A G C T G A T G C C C T G
(159) G T C C T C G T A G C A C G T G G C
(160) C C T G G T A T C T A T T T C A C A
(161) G C A C T T C C C A G C A A A T C C
(162) T T C G G G G C A C T G G C A C A C
(163) G A A A T C T G A G A A G T A C A G
(164) G G C C T G C T G G C A G G T G C C
(165) C C C G T T G A A A C A C C T T G G
(166) C T C G C T G C A A C T T T T G A C
(167) A G G C A G T G A G T G G C A C T G
(168) T G C C C T G C C A C T C T T G C A
(169) C C A G C A A T A T T C C A C C C G
(170) G T T G C T T C T G A G C A C A G G
(171) G C G C A G C C A T G A C T G A T G
(172) T T G C T G G T A T A T C A T G

Step 4

Preparation of Material C)

Substantially the same procedures as described in Step 13 of Referential Example 1 are repeated except that the transformant obtained in Step 3 of Referential Example 2 is used instead of the transformant used in Referential Example 1. Thus, there is obtained a polypeptide having the following amino acid sequence.

Met Ile Tyr Gln Gln His Gln Ser Trp Leu Arg Pro Val Leu Arg Ser Asn Arg Val Glu Tyr Cys Trp Cys Asn Ser Gly Arg Ala Gln Cys His Ser Val Pro Val Lys Ser Cys Ser Glu Pro Arg Cys Phe Asn Gly Gly Thr Cys Gln Gln Ala Leu Tyr Phe Ser Asp Phe Val Cys Gln Cys Pro Glu Gly Phe Ala Gly Lys Cys Cys Glu Ile Asp Thr Arg Ala Thr Cys Tyr Glu Asp Gln Gly Ile Ser Tyr Arg Gly Thr Trp Ser Thr Ala Glu Ser Gly Ala Glu Cys Thr Asn Trp Asn Ser Ser Ala Leu Ala Gln Lys Pro Tyr Ser Gly Arg Arg Pro Asp Ala Ile Arg Leu Gly Leu Gly Asn His Asn Tyr Cys Arg Asn Pro Asp Arg Asp Ser Lys Pro Trp Cys Tyr Val Phe Lys Ala Gly Lys Tyr Ser Ser Glu Phe Cys Ser Thr Pro Ala Cys Ser Glu Gly Asn Ser Asp Cys Tyr Phe Gly Asn Gly Ser Ala Tyr Arg Gly Thr His Ser Leu Thr Glu Ser Gly Ala Ser Cys Leu Pro Trp Asn Ser Met Ile Leu Ile Gly Lys Val Tyr Thr Ala Gln Asn Pro Ser Ala Gln Ala Leu Gly Leu Gly Lys His Asn Tyr Cys Arg Asn Pro Asp Gly Asp Ala Lys Pro Trp Cys His Val Leu Lys Asn Arg Arg Leu Thr Trp Glu Tyr Cys Asp Val Pro Ser Cys Ser Thr Cys Gly Leu Arg Gln Tyr Ser Gln Pro Gln Phe Arg Ile Lys Gly Gly Leu Phe Ala Asp Ile Ala Ser His Pro Trp Gln Ala Ala Ile Phe Ala Lys His Arg Arg Ser Pro Gly Glu Arg Phe Leu Cys Gly Gly Ile Leu Ile Ser Ser Cys Trp Ile Leu Ser Ala Ala His Cys Phe Gln Glu Arg Phe Pro Pro His His Leu Thr Val Ile Leu Gly Arg Thr Tyr Arg Val Val Pro Gly Glu Glu Glu Gln Lys Phe Glu Val Glu Lys Tyr Ile Val His Lys Glu Phe Asp Asp Asp Thr Tyr Asp Asn Asp Ile Ala Leu Leu Gln Leu Lys Ser Asp Ser Ser Arg Cys Ala Gln Glu Ser Ser Val Val Arg Thr Val Cys Leu Pro Pro Ala Asp Leu Gln Leu Pro Asp Trp Thr Glu Cys Glu Leu Ser Gly Tyr Gly Lys His Glu Ala Leu Ser Pro Phe Tyr Ser Glu Arg Leu Lys Glu Ala His Val Arg Leu Tyr Pro Ser Ser Arg Cys Thr Ser Gln His Leu Leu Asn Arg Thr Val Thr Asp Asn Met Leu Cys Ala Gly Asp Thr Arg Ser Gly Gly Pro Gln Ala Asn Leu His Asp Ala Cys Gln

Gly Asp Ser Gly Gly Pro Leu Val Cys Leu Asn Asp Gly Arg Met Thr Leu Val Gly Ile Ile Ser Trp Gly Leu Gly Cys Gly Gln Lys Asp Val Pro Gly Val Tyr Thr Lys Val Thr Asn Tyr Leu Asp Trp Ile Arg Asp Asn Met Arg Pro.

Substantially the same procedures as described in Step 14 of Referential Example 1 are repeated except that the above-obtained peptide is used instead of IFN-$\gamma$-(48–146). Thus, there is obtained a peptide in which the $\epsilon$-amino groups of lysines are converted into amidino groups.

What is claimed is:

1. A method for producing an active protein having at least methionine residue, arginine residue and lysine residue in its amino acid sequence at an intermediate portion between the N-terminal amino acid residue and the C-terminal amino acid residue of the active protein but not having a methionine residue as the N-terminal amino acid residue, which comprises:

(1) providing:

(a) a first peptide fragment having a first amino acid sequence corresponding to part of an active protein, said first amino acid sequence containing the N-terminal amino acid residue of the active protein, and (b) a second peptide fragment having a second amino acid sequence corresponding to the remaining part of the active protein, said second amino acid sequence containing the C-terminal amino acid residue of the active protein, at least one of said first peptide fragment and said second peptide fragment being one which has been obtained by a method using recombinant DNA technique, provided that in the case where said first peptide fragment is one which has been obtained by a method using recombinant DNA technique, said first peptide fragment is one which has been obtained by a method comprising producing a first predetermined peptide fragment by means of recombinant DNA technique and deleting from said first predetermined peptide fragment at its N-terminus at least one amino acid residue, and that in the case where said second peptide fragment is one which has been obtained by a method using recombinant DNA technique, said second peptide fragment is one which has been obtained by means of recombinant DNA technique or has been obtained by a method comprising producing a second predetermined peptide fragment by means of recombinant DNA technique and adding to said second predetermined peptide fragment at its N-terminus at least one amino acid residue, said first predetermined peptide fragment being a methionyl peptide containing the N-terminal amino acid residue of the active protein but not containing the peptide residue having an amino acid sequence of from the first occurring methionine residue subsequent to said N-terminal amino acid residue to the C-terminal amino acid residue of said active protein, said second predetermined peptide fragment being a peptide having an amino acid sequence of from the first occurring methionine residue subsequent to the N-terminal amino acid residue to the C-terminal amino acid residue of the active protein; and (2) linking said first peptide fragment at its C-terminus to said second peptide fragment at its N-terminus.

2. A method according to claim 1, wherein said first peptide fragment and said second peptide fragment are predetermined so that an amino acid residue attached to the C-terminus of said first peptide fragment is reactive with an amino acid residue attached to the N-terminus of said second peptide fragment but the reaction between the amino acid residue attached to the C-terminus of said first peptide fragment and the amino acid residue attached to the N-terminus of said second peptide fragment is not accompanied by a side reaction.

3. A method according to claim 2, wherein said side reaction is a racemization reaction.

4. A method according to claim 1, wherein said first peptide fragment and said second peptide fragment are predetermined so that a first occurring methionine residue subsequent to the N-terminal amino acid residue of the active protein constitutes the N-terminal amino acid residue of the amino acid sequence of said second peptide fragment.

5. A method according to claim 4, wherein the N-terminal amino acid residue of said first peptide fragment is an amino acid residue other than a methionine residue and said first peptide fragment is one which has been obtained by a method comprising producing a first predetermined peptide fragment having a methionine residue as the N-terminal amino acid residue by recombinant DNA technique and deleting said methionine residue as the N-terminal amino acid residue from said first predetermined peptide fragment.

6. A method according to claim 4, wherein said second peptide fragment is one obtained by recombinant DNA technique.

7. A method according to claim 1, wherein said first peptide fragment and said second peptide fragment are predetermined so that an amino acid residue positioned near the first occurring methionine residue subsequent to the N-terminal amino acid residue of the active protein on the side of the N-terminus of the active protein constitutes the N-terminal amino acid residue of said second peptide fragment and so that the C-terminal amino acid residue of said first peptide fragment has high reactivity with the N-terminal amino acid residue of said second peptide fragment.

8. A method according to claim 7, wherein said second peptide fragment is one which has been prepared by a method comprising producing by recombinant DNA technique a second predetermined peptide fragment of which the N-terminal amino acid residue is said first occurring methionine residue subsequent to the N-terminal amino acid residue of the active protein and adding at least one amino acid residue to the N-terminus of said second predetermined peptide fragment by organic synthesis.

9. A method according to claim 8, wherein the N-terminal amino acid residue of said first peptide fragment is an amino acid residue other than a methionine residue and said first peptide fragment is one which has been obtained by a method comprising producing a first predetermined peptide fragment having a methionine residue as the N-terminal amino acid residue by recombinant DNA technique and deleting said methionine residue as the N-terminal amino acid residue from said first predetermined peptide fragment.

10. A method according to claim 1, wherein the linking of said first peptide fragment to said second peptide fragment is conducted in the presence of a condensation agent.

11. A method according to claim 10, wherein said condensation agent is a chemical condensation agent or a protease.

12. A method according to claim 1, wherein at least one of an amino acid residue attached to the C-terminus of the first peptide fragment and an amino acid residue attached to the N-terminus of the second peptide fragment is converted to an activated form having a reactive group, followed by the linking of said first peptide fragment to said second peptide fragment.

13. A method according to claim 12, wherein said reactive group is an azido group or a reactive ester group.

14. A method according to claim 1, wherein one of said first peptide fragment and said second peptide fragment is relatively short in length of the amino acid sequence and the peptide fragment having a relatively short length of amino acid sequence is produced by organic synthesis.

15. A method according to claim 5, wherein said second peptide fragment is one obtained by recombinant DNA technique.

* * * * *